US006967242B2

(12) United States Patent
Swayze et al.

(10) Patent No.: US 6,967,242 B2
(45) Date of Patent: *Nov. 22, 2005

(54) ANTIMICROBIAL 2-DEOXYSTREPTAMINE COMPOUNDS

(75) Inventors: Eric Swayze, Carlsbad, CA (US); Richard H. Griffey, Vista, CA (US); Yili Ding, San Diego, CA (US); Venkatraman Mohan, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 14 days.

This patent is subject to a terminal disclaimer.

(21) Appl. No.: 10/299,220

(22) Filed: Nov. 19, 2002

(65) Prior Publication Data

US 2003/0109461 A1 Jun. 12, 2003

Related U.S. Application Data

(63) Continuation of application No. 09/452,606, filed on Dec. 1, 1999, now Pat. No. 6,541,456.

(51) Int. Cl.$^7$ .......................... C07H 15/22; C07H 17/04
(52) U.S. Cl. ..................... 536/13.2; 536/13.3; 536/16.6; 536/16.8
(58) Field of Search ............................. 514/36, 38, 40, 514/42, 53; 536/13.2, 13.3, 16.6, 16.8

(56) References Cited

U.S. PATENT DOCUMENTS

| 4,247,687 A | 1/1981 | Hanessian ..................... 536/12 |
| 5,942,547 A | 8/1999 | Gustafson et al. .......... 514/616 |
| 6,140,361 A | 10/2000 | Gustafson et al. .......... 514/488 |

FOREIGN PATENT DOCUMENTS

JP 55015445 2/1980

OTHER PUBLICATIONS

Greene, T. "Protective Groups in Organic Synthesis" John Wiley & Sons, 1981, pp 29–39.*

Alper, P.B. et al., "Probing the Specificity of Aminoglycoside–Ribosomal RNA Interactions with Designed Synthetic Analogs," *J. Am. Chem. Soc.*, 1998, 120, 1965–1978.

Ding, Y et al., "Efficient synthesis of neomycin B related aminoglycosides", *Tet Lett.*, 2000, 41, 4049–4052.

Greenberg, W.A. et al., "Design and synthesis of new aminoglycoside antibiotics containing neamine as an optimal core structure: correlation of antibiotic activity with in vitro inhibition of translation", *J. Am. Chem. Soc.*, 1999, 121, 6527–6541.

Kumar, V., et al., "Aminoglycoside antibiotics," *J. Org. Chem.*, 1981, 46, 4298–4230.

Moazed, D. et al., "Interaction of antibiotics with functional sites in 16S ribosomal RNA," *Nature*, 1987, 327, 389–394.

Tamura, J., et al., "The synthesis of destomycin C," 1988, 174, 181–199.

van Stratten, N., et al., "An expeditious route to the synthesis of adenophostin A," *Tetrahedron*, 1997, 53(18), 6509–6522.

* cited by examiner

*Primary Examiner*—James O. Wilson
*Assistant Examiner*—Leigh C. Maier
(74) *Attorney, Agent, or Firm*—ISIS Patent Department Woodcock Washburn LLP

(57) ABSTRACT

The present invention is directed to analogs of aminoglycoside compounds of the class having a glycosylated 2-deoxystreptamine (2-DOS) ring as well as their preparation and use as prophylactic or therapeutics against microbial infection. Compounds of the invention comprises at least one aryl, heteroaryl, substituted aryl or substituted heteroaryl group in place of a glycosyl group attached to the 2-deoxystreptamine ring.

16 Claims, 9 Drawing Sheets

2-Deoxystreptamine (2-DOS)

Neomycin B

Paromomycin

Lividomycin

Tobramycin

Bekanamycin

Ribostamycin

Kanamycin A and B

Gentamycin $C_1$, $C_{1a}$ and $C_2$

Sisomycin

ANTIMICROBIAL 2-DEOXYSTREPTAMINE COMPOUNDS

This application is a continuation of U.S. patent application Ser. No. 09/452,606, filed Dec. 1, 1999, now U.S. Pat. No. 6,541,456.

FIELD OF THE INVENTION

The present invention is directed to aminoglycoside compounds and in particular to aryl substituted aminoglycosides and synthetic methods for their preparation and use as therapeutic or prophylactic agents.

BACKGROUND OF THE INVENTION

A particular interest in modem drug discovery is the development of novel low molecular weight orally-bioavailable drugs that work by binding to RNA. RNA, which serves as a messenger between DNA and proteins, was thought to be an entirely flexible molecule without significant structural complexity. Recent studies have revealed a surprising intricacy in RNA structure. RNA has a structural complexity rivaling proteins, rather than simple motifs like DNA. Genome sequencing reveals both the sequences of the proteins and the mRNAs that encode them. Since proteins are synthesized using an RNA template, such proteins can be inhibited by preventing their production in the first place by interfering with the translation of the mRNA. Since both proteins and the RNAs are potential drug targeting sites, the number of targets revealed from genome sequencing efforts is effectively doubled. These observations unlock a new world of opportunities for the pharmaceutical industry to target RNA with small molecules.

Classical drug discovery has focused on proteins as targets for intervention. Proteins can be extremely difficult to isolate and purify in the appropriate form for use in assays for drug screening. Many proteins require post-translational modifications that occur only in specific cell types under specific conditions. Proteins fold into globular domains with hydrophobic cores and hydrophilic and charged groups on the surface. Multiple subunits frequently form complexes, which may be required for a valid drug screen. Membrane proteins usually need to be embedded in a membrane to retain their proper shape. The smallest practical unit of a protein that can be used in drug screening is a globular domain. The notion of removing a single alpha helix or turn of a beta sheet and using it in a drug screen is not practical, since only the intact protein may have the appropriate 3-dimensional shape for drug binding. Preparation of biologically active proteins for screening is a major limitation of classical high throughput screening and obtaining biologically active forms of proteins is an expensive and limiting reagent in high throughput screening efforts.

For screening to discover compounds that bind RNA targets, the classic approaches used for proteins can be superceded with new approaches. All RNAs are essentially equivalent in their solubility, ease of synthesis or use in assays. The physical properties of RNAs are independent of the protein they encode. They may be readily prepared in large quantity through either chemical or enzymatic synthesis and are not extensively modified in vivo. With RNA, the smallest practical unit for drug binding is the functional subdomain. A functional subdomain in RNA is a fragment that, when removed from the larger RNA and studied in isolation, retains its biologically relevant shape and protein or RNA-binding properties. The size and composition RNA functional subdomains make them accessible by enzymatic or chemical synthesis. The structural biology community has developed significant experience in identification of functional RNA subdomains in order to facilitate structural studies by techniques such as NMR spectroscopy. For example, small analogs of the decoding region of 16S rRNA (the A-site) have been identified as containing only the essential region, and have been shown to bind antibiotics in the same fashion as the intact ribosome.

The binding sites on RNA are hydrophilic and relatively open as compared to proteins. The potential for small molecule recognition based on shape is enhanced by the deformability of RNA. The binding of molecules to specific RNA targets can be determined by global conformation and the distribution of charged, aromatic, and hydrogen bonding groups off of a relatively rigid scaffold. Properly placed positive charge are beleived to be important, since long-range electrostatic interactions can be used to steer molecules into a binding pocket with the proper orientation. In structures where nucleobases are exposed, stacking interactions with aromatic functional groups may contribute to the binding interaction. The major groove of RNA provides many sites for specific hydrogen bonding with a ligand. These include the aromatic N7 nitrogen atoms of adenosine and guanosine, the O4 and O6 oxygen atoms of uridine and guanosine, and the amines of adenosine and cytidine. The rich structural and sequence diversity of RNA suggests to us that ligands can be created with high affinity and specificity for their target.

Although our understanding of RNA structure and folding, as well as the modes in which RNA is recognized by other ligands, is far from being comprehensive, significant progress has been made in the last decade (Chow, C. S.; Bogdan, F. M., Chem. Rev., 1997, 97, 1489, Wallis, M. G.; Schroeder, R., Prog. Biophys. Molec. Biol. 1997, 67, 141). Despite the central role RNA plays in the replication of bacteria, drugs that target these pivotal RNA sites of these pathogens are scarce. The increasing problem of bacterial resistance to antibiotics make the search for novel RNA binders of crucial importance.

Certain small molecules can bind RNA and block essential functions of the bound RNA. Examples of such molecules include erythromycin, which binds to bacterial rRNA and releases peptidyl-tRNA and mRNA, and the aminoglycoside antibiotics. Aminoglycoside antibiotics have long been known to bind RNA. They exert their antibacterial effects by binding to specific target sites in the bacterial ribosome. For the structurally related antibiotics neamine, ribostamycin, neomycin B, and paromomycin, the binding site has been localized to the A-site of the prokaryotic 16S ribosomal decoding region RNA (Moazed, D.; Noller, H. F., Nature, 1987, 327, 389). Binding of aminoglycosides to this RNA target interferes with the fidelity of mRNA translation and results in miscoding and truncation, leading ultimately to bacterial cell death (Alper, P. B.; Hendrix, M.; Sears, P.; Wong, C., J. Am. Chem. Soc., 1998, 120, 1965).

There is a need in the art for new chemical entities that work against bacteria with broad-spectrum activity. Perhaps the biggest challenge in discovering RNA-binding antibacterial drugs is identifying vital structures common to bacteria that can be disabled by small molecule drug binding. A challenge in targeting RNA with small molecules is to develop a chemical strategy which recognizes specific shapes of RNA. There are three sets of data that provide hints on how to do this: natural protein interactions with RNA, natural product antibiotics that bind RNA, and man-made RNAs (aptamers) that bind small molecules. Each data set, however, provides different insights to the problem.

Several classes of drugs obtained from natural sources have been shown to work by binding to RNA or RNA/protein complexes. These include three different structural classes of antibiotics: thiostreptone, the aminoglycoside family and the macrolide family of antibiotics. These examples provide powerful clues to how small molecules and targets might be selected. Nature has selected RNA targets in the ribosome, one of the most ancient and conserved targets in bacteria. Since antibacterial drugs are desired to be potent and have broad-spectrum activity these ancient processes fundamental to all bacterial life represent attractive targets. The closer we get to ancient conserved functions the more likely we are to find broadly conserved RNA shapes. It is important to also consider the shape of the equivalent structure in humans, since bacteria were unlikely to have considered the therapeutic index of their RNAs while evolving them.

A large number of natural antibiotics exist, these include the aminoglycosides, kirromycin, neomycin, paromomycin, thiostrepton, and many others. They are very potent, bactericidal compounds that bind RNA of the small ribosomal subunit. The bactericidal action is mediated by binding to the bacterial RNA in a fashion that leads to misreading of the genetic code. Misreading of the code while translating integral membrane proteins is thought to produce abnormal proteins that compromise the barrier properties of the bacterial membrane.

Antibiotics are chemical substances produced by various species of microorganisms (bacteria, fungi, actinomycetes) that suppress the growth of other microorganisms and may eventually destroy them. However, common usage often extends the term antibiotics to include synthetic antibacterial agents, such as the sulfonamides, and quinolines, that are not products of microbes. The number of antibiotics that have been identified now extends into the hundreds, and many of these have been developed to the stage where they are of value in the therapy of infectious diseases. Antibiotics differ markedly in physical, chemical, and pharmacological properties, antibacterial spectra, and mechanisms of action. In recent years, knowledge of molecular mechanisms of bacterial, fungal, and viral replication has greatly facilitated rational development of compounds that can interfere with the life cycles of these microorganisms.

At least 30% of all hospitalized patients now receive one or more courses of therapy with antibiotics, and millions of potentially fatal infections have been cured. At the same time, these pharmaceutical agents have become among the most misused of those available to the practicing physician. One result of widespread use of antimicrobial agents has been the emergence of antibiotic-resistant pathogens, which in turn has created an ever-increasing need for new drugs. Many of these agents have also contributed significantly to the rising costs of medical care.

When the antimicrobial activity of a new agent is first tested a pattern of sensitivity and resistance is usually defined. Unfortunately, this spectrum of activity can subsequently change to a remarkable degree, because microorganisms have evolved the array of ingenious alterations discussed above that allow them to survive in the presence of antibiotics. The mechanism of drug resistance varies form microorganism to microorganism and from drug to drug.

The development of resistance to antibiotics usually involves a stable genetic change, heritable from generation to generation. Any of the mechanisms that result in alteration of bacterial genetic composition can operate. While mutation is frequently the cause, resistance to antimicrobial agents may be acquired through transfer of genetic material from one bacterium to another by transduction, transformation or conjugation.

For the foregoing reasons, there is a need for new chemical entities that possess antimicrobial activity. Further, in order to accelerate the drug discovery process, new methods for synthesizing aminoglycoside antibiotics are needed to provide an array of compounds that are potentially new drugs for the treatment microbial infections.

SUMMARY OF THE INVENTION

In an aspect of the present invention there are provided compounds of the formula (I):

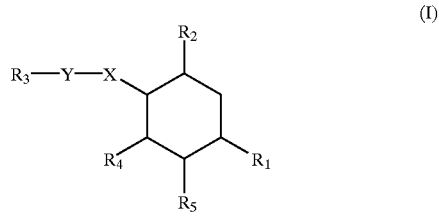

(I)

wherein,
$R_1$ and $R_2$ are independently amino or protected amino;
X is O, S, or NH;
Y is a bond or a divalent linking group;
$R_3$ is aryl, heteroaryl, substituted aryl or substituted heteroaryl; and
one of $R_4$ and $R_5$ is hydroxyl or protected hydroxyl, and the other is selected from the group consisting of formula (II), (III) and (IV):

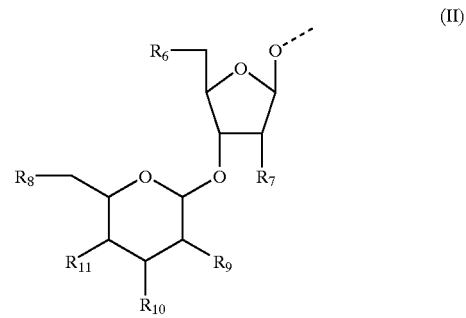

(II)

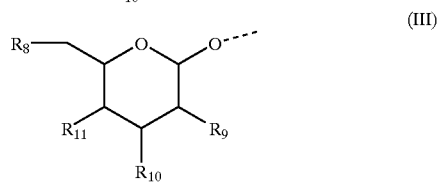

(III)

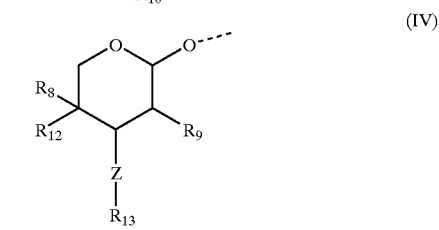

(IV)

wherein
$R_6$ and $R_7$ are independently hydroxyl or protected hydroxyl;
$R_8$, $R_9$, $R_{10}$, and $R_{11}$ are independently hydroxyl, protected hydroxyl, amino or protected amino;
$R_{12}$ and $R_{13}$ are independently H or alkyl; and
Z is O, S or NH.

BRIEF DESCRIPTION OF THE FIGURES

These and other features, aspects, and advantages of the present invention will become better understood with reference to the following description and accompanying drawings where.

DETAILED DESCRIPTION OF THE INVENTION

Aspects of the present invention are directed to aminoglycoside compounds having a common 2-deoxystreptamine (2-DOS) moiety (as shown in FIG. 1), and their use as therapeutic and/or prophylactic agents as well as processes and intermediates for making them. Aminoglycosides of the invention have at least one glycosyl group attached to the 2-DOS ring replaced by an aryl or heteroaryl group. In a preferred embodiment the glycosyl group at the 4-position of the 2-DOS ring is replaced with an aryl or heteroaryl group so as to produce a 2-DOS compound having such group covalently bound at its 4-position, 5-position, or 6-position.

Paromomycin, lividomycin and neomycin B are aminoglycoside antibiotics that have a 4,5-substituted 2-DOS ring system as is shown in FIG. 1. In a preferred embodiment of the present invention, the "A-ring" (the glycosyl group at the 4-position of the 2-DOS ring) is replaced with an aromatic including heteroaromatic moiety. Likewise, the glycosyl ring at the 4-position of tobramycin, kanamycin, gentamycin, ribostamycin, amikacin, sisomycin, butirosin, gentamycin, hygromycin and apramycin are replaced with an aromatic moiety as defined herein.

While not being bound by theory, replacing the 4-position glycosyl ring with an aromatic moiety (aryl or heteroaryl) improves binding to its target RNA due to an stacking interaction with a bulged guanine residue. Furthermore, the presence of an aromatic group may also improve lipophilicity, providing the potential for improved pharmacokinetic parameters.

Figure 1A:
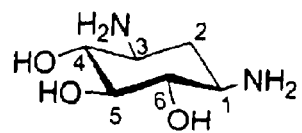
FIGS. 1a, 1b and 1c are structural illustrations of 2-deoxystreptamine (2-DOS) and various aminoglycosides incorporating a 2-DOS ring.
Figure 1A:
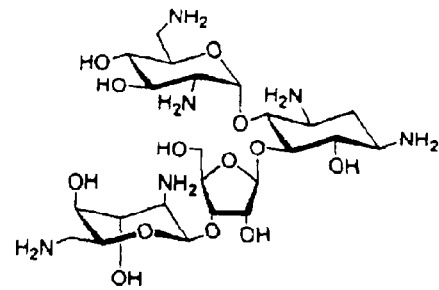
Figure 1A:
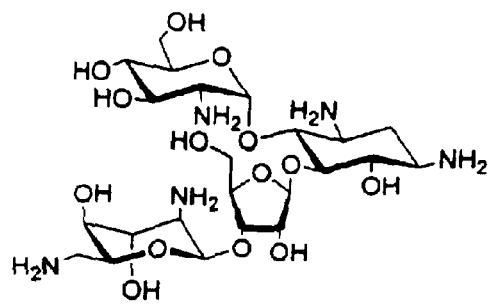
Figure 1A:
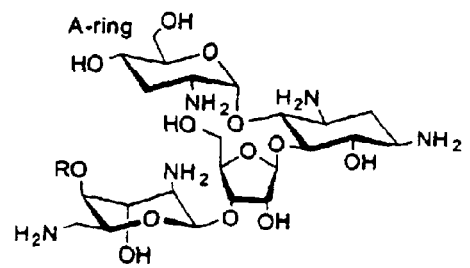
Figure 1A:
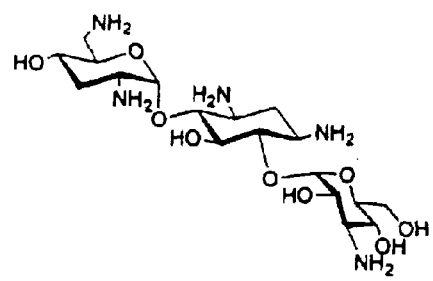
Figure 1B:
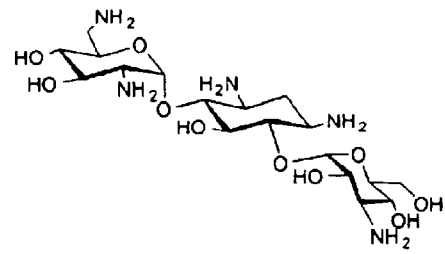
Figure 1B:
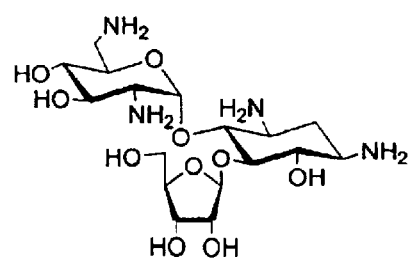
Figure 1B:
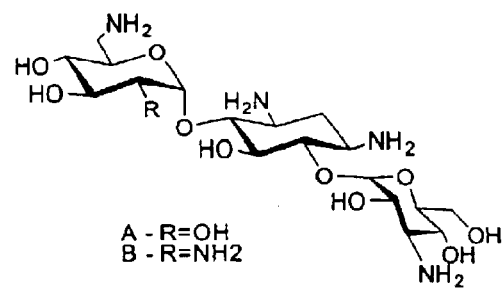
Figure 1C:
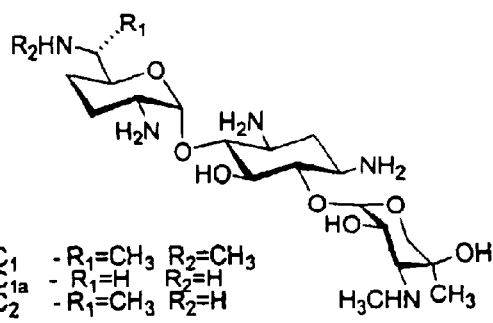
Figure 1C:
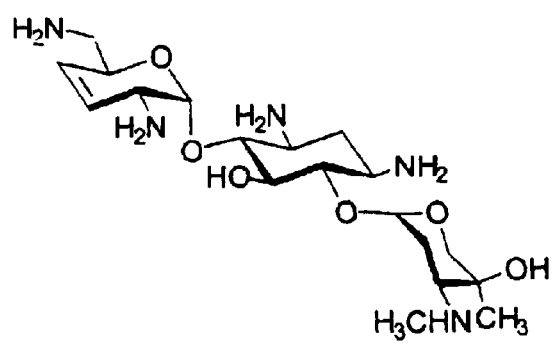
Figure 2:
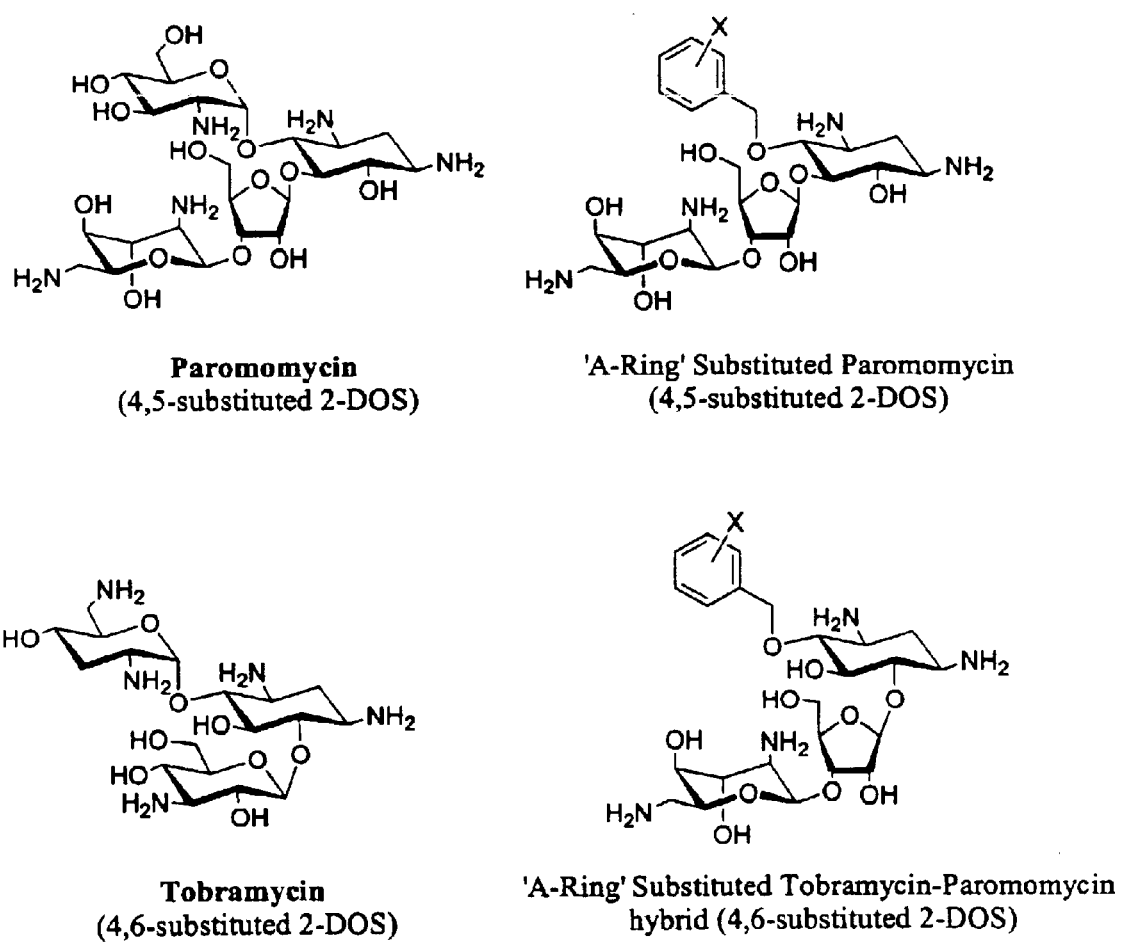
FIG. 2 is a structural illustration of A-ring substituted aminoglycoside analogs.

Tobramycin is an aminoglycoside antibiotic that has a 4,6-substituted 2-DOS ring system as is shown in FIG. 2.

In a preferred embodiment of the present invention, the glycosyl ring at the 4-position of the 2-DOS ring of tobramycin is replaced with an aromatic moiety.

In an alternative aspect, aminoglycoside compounds of the invention have the general formula (I):

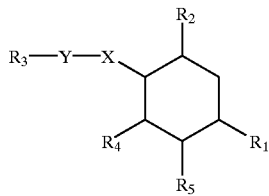

(I)

wherein X, Y, Z and $R_1$ through $R_5$ are as previously defined.

X can be O, S, NH or $CH_2$. In a preferred embodiment X is O.

Y can be a bond or a divalent linking group between the heteroatom X and the group $R_3$. In a preferred embodiment Y is a bond. In an alternative embodiment, Y is a divalent aliphatic chain of 1–10 carbon atoms such as methylene, ethylene or propylene. Y may also be a carbonyl (C=O) or thiocarbonyl (C=S) group. Y and X together may form an amide, thioamide, ether, thioether, amidino, guanidino, ester or thioester group.

Z can be O, S, or NH. In a preferred embodiment Z is NH.

$R_1$ and $R_2$ are independently amino ($NH_2$) or protected amino. Protected amino groups are known and used in the synthetic organic chemistry art and include but are not limited to t-butoxycarbonyl (BOC), benzyloxycarbonyl (Cbz), azide (N3), 2-trimethylsilylethoxy-carbonyl (Teoc), triphenylmethyl-sulfenyl, 1-methyl-1-(4-biphenylyl) ethoxycarbonyl (Bpoc), allyloxycarbonyl (Alloc), 9-fluorenylmethyloxy-carbonyl (Fmoc), amide groups, such as formyl, acetyl, trihaloacetyl, benzoyl, and nitrophenylacetyl, sulfonamide groups, such as 2-nitrobenzenesulfonyl, imine- and cyclic imide groups, such as phthalimido and dithiasuccinoyl. Further examples of protected amino groups are described by Greene and Wuts in *Protective Groups in Organic Synthesis,* 2d edition (John Wiley & Sons, New York, 1991) as well as conditions for their preparation and removal or conversion back to an amino group. A preferred protected amino group is an azide ($N_3$) which may be formed upon reacting an amino group with triflic azide. The azide may be converted back to amino upon reacting with trimethylphosphine. In a particular embodiment, $R_1$ and $R_2$ are both $N_3$. In a more preferred embodiment both $R_1$ and $R_2$ are $NH_2$.

$R_3$ is aryl, heteroaryl, substituted aryl or substituted heteroaryl. Aryl groups include, but are not limited to, phenyl, tolyl, benzyl, naphthyl, anthracyl, phenanthryl, and xylyl. Heteroaryl groups suitable for the invention include but are not limited to pyrrole, furan, thiophene, pyrazole, imidazole, triazole, tetrazole, oxazole, oxadiazole, thiazole, thiadiazole, indole, carbazole, benzofuran, benzothiophene, indazoles, benzimidazole, benzotriazole, benzoxazole, benzothiazole, benzothiadiazole, purine, pyridine, pyridazine, pyrimidine, pyrazine, triazine, quinoline, acridine, isoquinoline, cinnoline, phthalazine, quinazoline, quinoxaline, phenazine, phenanthroline and others.

Substituent groups for the above aryl and heteroaryl groups include but are not limited to halogen (fluoro, chloro, bromo, iodo), hydroxyl (OH), thiol (SH), carboxy (COOH), aliphatic chain (straight, branch, saturated or unsaturated), carbocycle (saturated or unsaturated), carboxy ester (COOR), carboxamide (CONHR where R is hydrogen, aliphatic, carbocyclic, aryl or a heteroaryl group), aldehyde (CHO), keto (C=O), oxo (=O), nitrile (CN), amidine ($C(NH)NH_2$), guanidine ($NH—C(NH)NH_2$), trifluoromethyl ($CF_3$), trifluoromethoxy ($OCF_3$), alkyloxy, ether, aryloxy, S-alkyl, thioether, disulfide, S-aryl or amino including NH-alkyl, N-(alkyl)$_2$, NH-aryl and amino (NH$_2$) and nitro (NO$_2$), aryl and heteroaryl.

Aliphatic groups suitable for use in the invention include but are not limited to saturated and unsaturated, straight or branched, substituted or unsubstituted, alkyl, alkenyl and alkynyl groups including (C$_1$–C$_{10}$) methyl, ethyl, propyl, butyl, pentyl, hexyl, heptyl, octyl, nonyl, decyl and other higher straight-chain alkyl groups; isopropyl, isobutyl, sec-butyl, tert-butyl, 1,1,2-trimethylpropyl, 2-methyl-propyl, 2-methyl-4-ethylbutyl, 2,4-diethylpropyl, 3-propyl-butyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched-chain groups; vinyl, allyl, crotyl, propargyl, 2-pentenyl and other unsaturated groups.

Carbocyclic groups suitable for the invention include but are not limited to cyclopropyl, cyclopentyl and cyclohexyl and other carbocyclic groups. Preferred saccharides (mono, di, tri) according to the invention include furanose and pyranose sugars wherein the hydroxyl groups may be replaced with amino or protected amino groups.

Heterocyclic groups suitable for use in the invention include both non-aromatic heterocycles and aromatic heterocycles. Non-aromatic heterocycle groups suitable for the invention include but are not limited to epoxide, oxetane, tetrahydrofuran, tetrahydropyran, dihydropyran, dioxane, trioxane, ethylenesulfide, thietane, tetrahydrothiophene, tetrahydrothiopyran, dithiane, trithiane, aziridine, azetidine, pyrrolidine, piperidine, homopiperidine, piperazine, homopiperazine, triazine, quinuclidine, decahydroquinoline, oxazole, morpholine, thiazolidine, thiomorpholine, gamma-butyrolactone, delta-valerolactone, thiolactone and others.

The aliphatic, carbocyclic and heterocyclic groups may be substituted with any of the aryl and heteroaryl R$_3$ substituents.

In a preferred embodiment, the aryl or heteroaryl group R$_3$ is substituted with one or more groups selected from the group consisting of OH, SH, Cl, F, Br, I, CN, NH$_2$, NO$_2$, amidine, guanidine, COOH, C$_{1-8}$ alkyl, C$_{2-8}$ alkenyl, C$_{2-8}$ alkynyl, CF$_3$, OCF$_3$, saturated or unsaturated carbocycle, saturated or unsaturated heterocycle, aryl, heteroaryl, OR$_{14}$, SR$_{14}$, NHR$_{14}$, N(R$_{14}$)$_2$, C(S)R$_{14}$, C(O)R$_{14}$ C(O)NHR$_{14}$, C(O)OR$_{14}$, OC(O)R$_{14}$, wherein R$_{14}$ is hydrogen, C$_{1-8}$ alkyl, C$_{2-8}$ alkenyl, C$_{2-8}$ alkynyl (wherein alkyl, alkenyl and alkynyl are straight or branched), carbocyclic (saturated or unsaturated), heterocyclic (saturated or unsaturated), aryl or a heteroaryl group. In particularly preferred embodiments R$_3$ is substituted with NH$_2$, OH, F, Cl, methoxy, keto/oxo (=O) or carboxy.

In particularly preferred embodiments R$_3$—Y— is selected from:

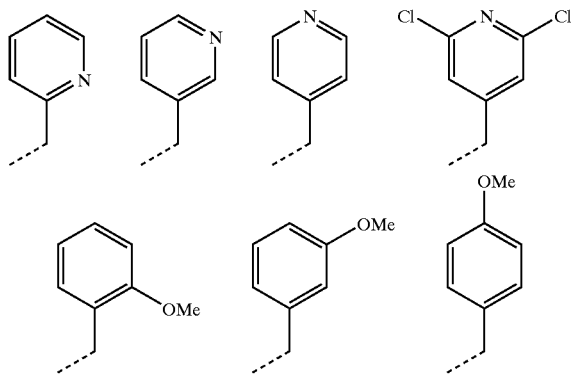

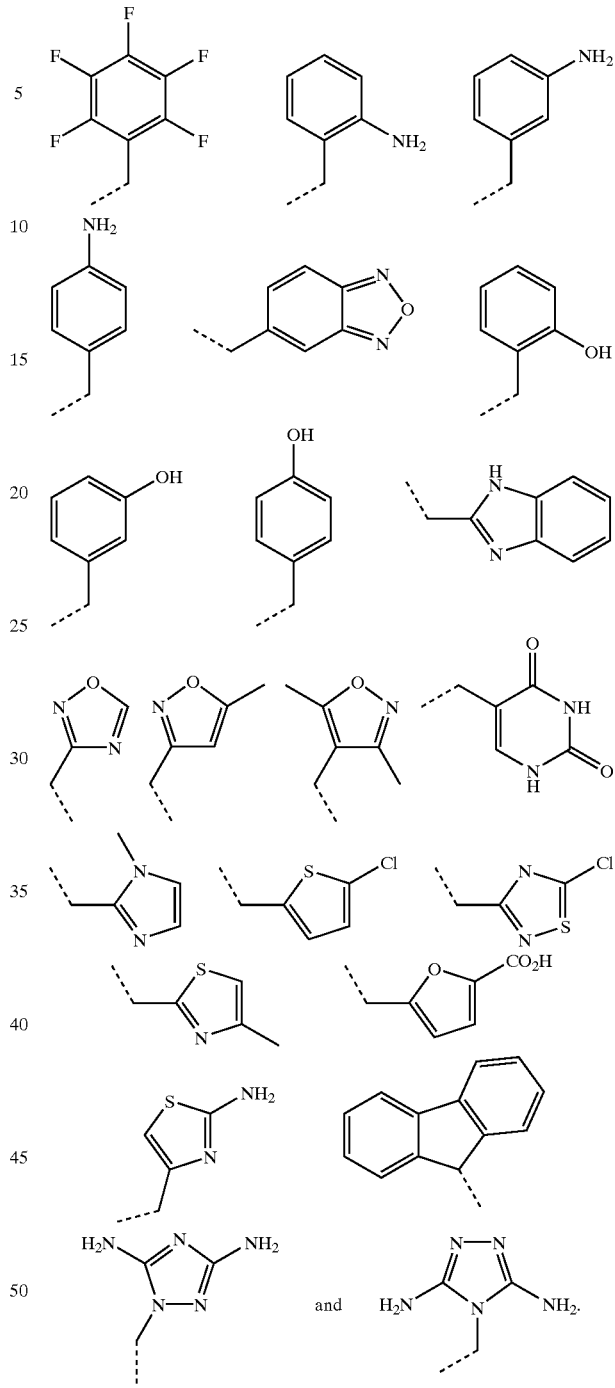

One of R$_4$ and R$_5$ is hydroxyl or protected hydroxyl. Any protected hydroxyl group known in the art of synthetic organic chemistry can be used, including but not limited to t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, pivavoyloxymethyl (POM), diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. A preferred protected hydroxyl group is acetyl. Further protected hydroxyl groups and their preparation and removal (or conversion to back to hydroxyl) are described by Greene and Wuts (supra). The other of $R_4$ and $R_5$ is selected from the group consisting of formula (II), (III) and (IV):

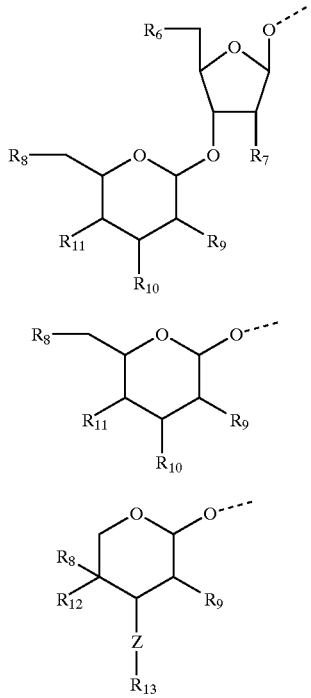

wherein $R_6$ and $R_7$ are independently hydroxyl or protected hydroxyl; $R_8$, $R_9$, $R_{10}$, and $R_{11}$ are independently hydroxyl, protected hydroxyl, amino or protected amino; $R_{12}$ and $R_{13}$ are independently H or alkyl; and Z is O, S or NH.

In a particular embodiment one of $R_4$ and $R_5$ is the group of formula (II). In this instance $R_6$, $R_7$, $R_{10}$ and $R_{11}$ are preferably hydroxyl; and $R_8$ and $R_9$ are independently amino or protected amino and more preferably amino. In a more preferred embodiment the group of formula (II) has the stereochemistry as defined by formula (IIa)

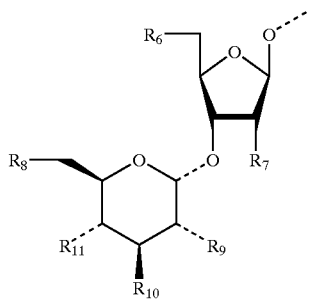

In another particular embodiment, one of $R_4$ and $R_5$ is the group of formula (III). In this instance $R_8$, $R_9$ and $R_{11}$ are each hydroxyl and $R_{10}$ is amino or protected amino and more preferably amino. In a more preferred embodiment, the group of formula (III) has the stereochemistry as defined by formula (IIIa)

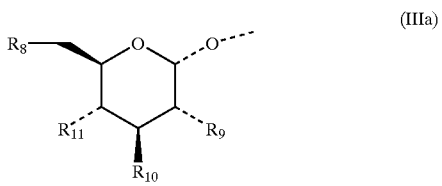

In another particular embodiment, one of $R_4$ and $R_5$ is the group of formula (IV). In this instance Z is NH; $R_8$ and $R_9$ are both hydroxyl or protected hydroxyl, preferably hydroxyl; and $R_{12}$ and $R_{13}$ are both methyl. In a more preferred embodiment, the group of formula (IV) has the stereochemistry as defined by formula (IVa)

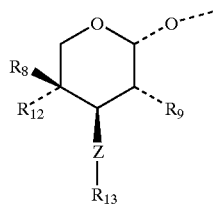

Compounds of the invention may be prepared according to established synthetic organic chemistry techniques. In a particular general method, 2-deoxystreptamine (2-DOS) is prepared from the hydrolysis of commercially available neomycin B. 2-DOS is derivatized at the 4-position with an aryl or heteroaryl group as defined by Y and $R_3$. The derivatized 2-DOS intermediate is subsequently glycosylated at the 5- or 6-position with a glycosyl donor corresponding to various aminoglycoside antibiotics, for example neobiosamine from neomycin B.

Preparation of the derivatized 2-DOS intermediate is believed to require protecting the amino and hydroxyl groups. In a preferred embodiment, the amino groups are protected by reacting the 2-DOS with triflic azide to give azide groups at the 1- and 3-positions. The hydroxyl groups at the 5- and 6-positions are protected by reacting the 2-DOS ring with 2,2-dimethoxy-propane to give an isopropylidine intermediate. The remaining free hydroxyl group at the 4-position is used as a functional group for appending the various aryl and heteroaryl groups to the 2-DOS ring.

The hydroxyl group may be reacted with an aryl or heteroaryl group that has a leaving group (e.g. halogen) to form an ether linkage wherein X is O, Y is a bond and $R_3$ is aryl or heteroaryl. Further, the aryl or heteroaryl group may have a linking group pending therefrom such as an alkyl chain wherein the leaving group is attached to the linking group thereby forming an ether linkage wherein Y is an alkylene linking group to the aryl or heteroaryl group $R_3$.

The 4-position hydroxyl of the protected 2-DOS intermediate may be converted into a leaving group by methods known in the art of organic chemistry. For example, treatment of the 4-hydroxyl protected 2-DOS with methanesulfonyl chloride and triethylamine or pyridine gives the 4-mesylate derivative. Treatment of the 4-hydroxyl protected 2-DOS with para-toluenesulfonyl chloride and triethylamine or pyridine give the 4-tosylate derivative. Treatment of the 4-hydroxyl protected 2-DOS with triphenylphosphine and either N-bromosuccinimide or carbon tetrabromide gives the 4-bromo derivative. All of these leaving groups are capable of being displaced by a nucleophile. For example, treatment of the 4-leaving group derivatives with Grignard reagents (e.g. phenylmagnesium bromide, benzylmagnesium bromide, phenethylmagnesium bromide) gives the 4-substituted phenyl, benzyl, or phenethyl protected 2-DOS derivatives, respectively. In addition, treatment of the 4-leaving group derivatives with thiols (e.g. benzenethiol, benzylmercaptan, benzeneethanthiol) and a suitable base (e.g. sodium hydride) gives the 4-thiol substituted phenyl, benzyl, or phenethyl protected 2-DOS derivatives, respectively. It should be noted that these sulfides are capable of being oxidized (with, for example, mCPBA or Oxone™) to the sulfoxides or sulfones.

The 4-position hydroxyl group of the protected 2-DOS intermediate may be oxidized to form a carbonyl group. A conventional way to oxidize alcohols to their carbonyl compounds is by a Swern or a PCC oxidation. The resulting carbonyl compound may be further elaborated by a carbon-carbon, a carbon-sulfur or a carbon-nitrogen bond forming reaction. These resulting carbon, sulfur or nitrogen containing linking groups may be attached to an aryl or heteroaryl group. For example, carbonyl groups readily undergo carbon-carbon double bond formation by a Wittig reaction. Treatment of the 4-carbonyl protected 2-DOS derivative with benzyltriphenylphosphonium bromide and a suitable base followed by reduction of the double bond by a hydrogenation gives the 4-benzyl-1,3-diamino-5,6-isopropylidine 2-DOS derivative.

The 4-carbonyl group can also undergo a reductive amination sequence with an amine to give a nitrogen containing linking group. Treatment of the 4-carbonyl protected 2-DOS derivative with an amine (aniline, benzylamine, phenethylamine) gives the corresponding imine which is subsequently reduced by treatment with sodium cyanoborohydride to give the 4-amino substituted phenyl, benzyl, or phenethyl protected 2-DOS derivatives, respectively.

Once the 2-DOS ring is derivatized at the 4-position, the hydroxyl protecting group(s) at the 5- and 6-position may be removed leaving free hydroxyl groups for glycosylation. For example, isopropylidine can be removed by mild acidolysis.

The deprotected derivatized 2-DOS ring may be glycosylated with a glycosyl donor selected from groups including but not limited to:

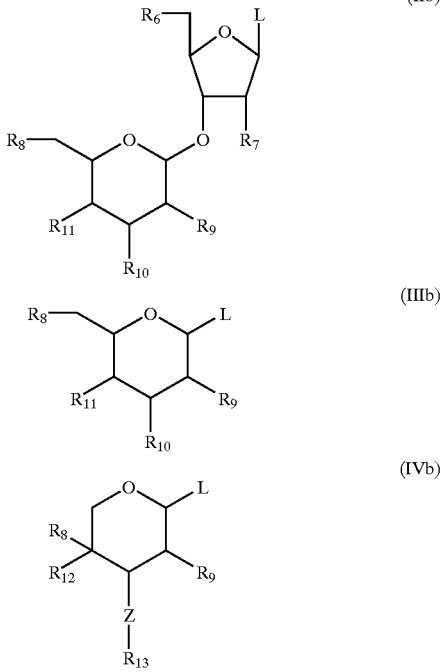

wherein L is a leaving group. A preferred leaving group is acetyl. Alternatively, L-may be a thio leaving group such as SR wherein R is alkyl, aryl or substituted aryl. Preferably R is methyl, ethyl, phenyl or p-methylphenyl. A thio leaving group may be prepared from an acetylated hydroxyl on the glycosyl donor by reacting with the corresponding thiol HS—R wherein R is as previously defined or by reacting with a disulfide reagent $(Me)_3Si$—S—SR. In this instance coupling may be achieved by reacting the thioglycosyl donor with the derivatized 2-DOS acceptor in the presence of N-iodosuccinimide (NIS) and triflic acid.

Glycosyl donors may be prepared by established synthetic chemistry techniques from commercially available starting materials or may be prepared from natural sources. For example, 2-DOS aminoglycosides can be hydrolyzed in whole or in part under acidic conditions to remove the 2-DOS ring from the glycosyl groups. The desired glycosyl intermediate is isolated and then reacted to place a leaving group at the appropriate position for subsequent coupling with the derivatized 2-DOS ring of the invention. In a preferred embodiment, the donor glycosyl intermediate is reacted with acetic anhydride in pyridine, which acetylates each of the hydroxyl groups. The glycosyl donor may then be coupled at its anomeric carbon with the derivatized 2-DOS ring in the presence of a Lewis acid such as trimethylsilyltriflate (TMSOTf). Alternatively, the acetyl group at the anomeric hydroxyl group of the glycosyl donor may be converted to other leaving groups such as halogens (Br, Cl, and F), thioethers (SR wherein R is alkyl, aryl or substituted aryl), sulfonyls (S(O)R).

Figure 3:
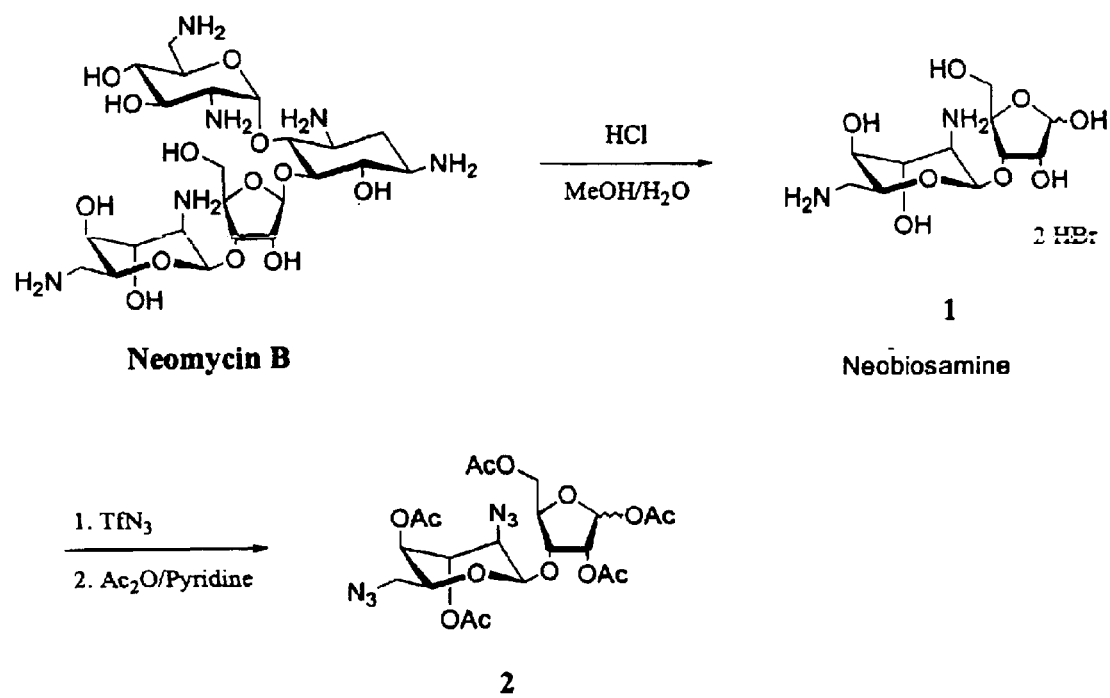
FIG. 3 is a schematic representation for the preparation of the glycosyl donor neobiosamine.
Figure 4:
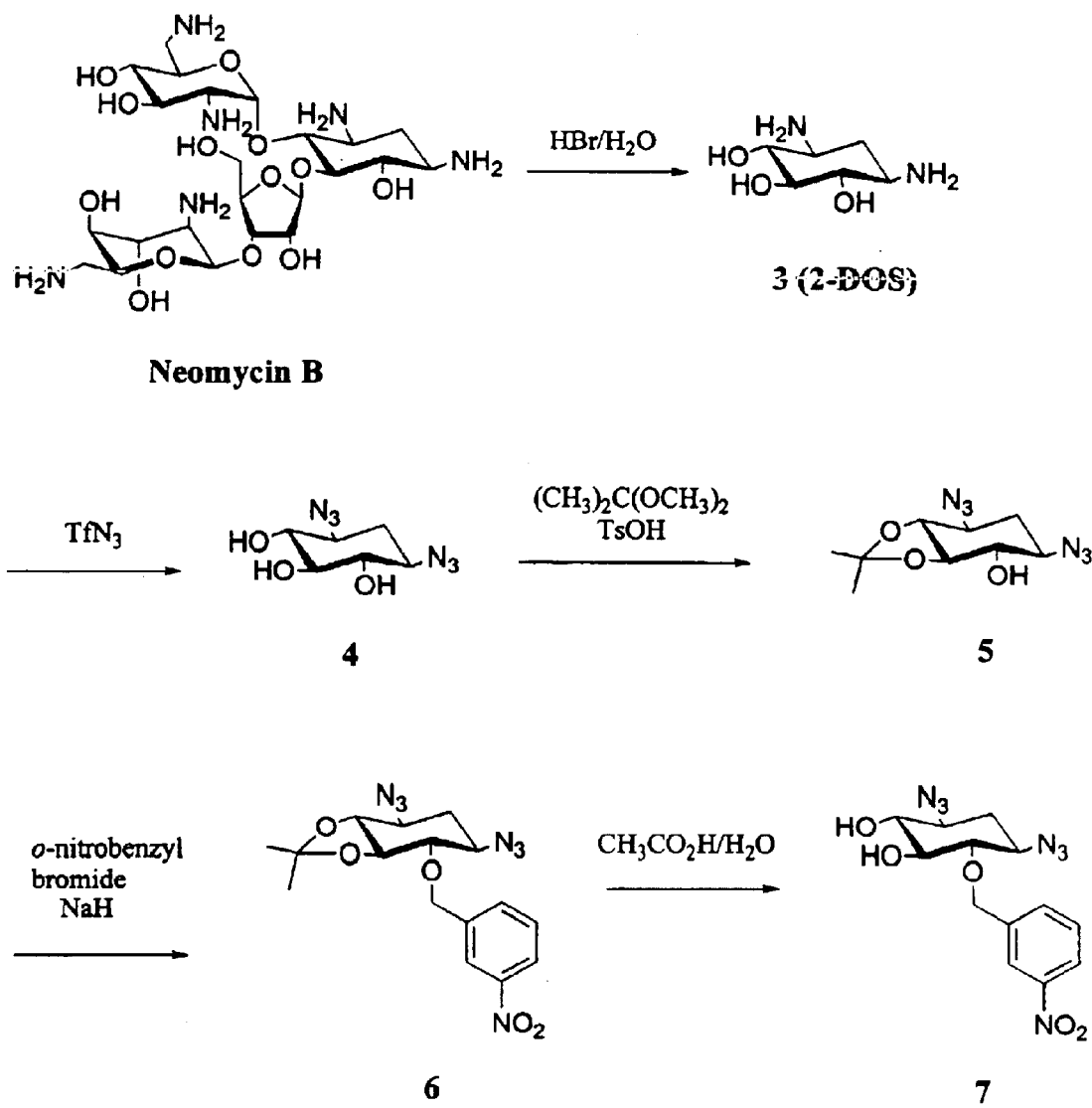
FIG. 4 is a schematic representation for the preparation of a 2-DOS glycosyl acceptor.

In a particular embodiment, neomycin B (neomycin sulfate) is degraded into its building blocks, neobiosamine 1 and neamine as is described in Examples 1 and Example 3 and shown in FIG. 3 and FIG. 4, respectively. The ease of isolation of neobiosamine 1 by these processes are particularly attractive. The unusual L-idose sugar present in neobiosamine 1, requires 15–20 synthetic steps to prepare via other routes. The amine groups of neobiosamine 1 are protected by conversion into the corresponding azides with triflic azide, and the hydroxyl groups acetylated with acetic anhydride and pyridine to give the glycosyl donor 2 as is described in Example 2 and shown in FIG. 3. This simple 3-step process gives the glycosyl donor 2 in good yields (~58%) in a very straightforward manner.

In a preferred embodiment of the invention, 2-deoxystreptamine 3 (2-DOS) is obtained via the degradation of neomycin B 1 as is described in Example 3 and shown in FIG. 3. By employing harsher conditions (48% HBr), neomycin B is completely degraded, and 2-deoxystreptamine 3 (2-DOS) can be isolated in good yields (~61%).

In preferred embodiments of the invention the amine groups of 2-deoxystreptamine 3 (2-DOS) are protected as the azides with triflic azide to give the di-azido compound 4 as is described in Example 4 and shown in FIG. 4. Two of the hydroxyl groups in the diazido azido compound 4, are protected as the isopropylidine derivative to give alcohol 5 as described in Example 5 and shown in FIG. 4. The remaining free hydroxyl group is readily alkylated upon treatment with an electrophile. For example, treatment of the alcohol 5 with base (NaH) and 3-nitrobenzyl bromide gives the aryl compound 6 as is described in Example 6 and shown in FIG. 4. The isopropylidine group in the aryl compound 6 is readily removed under mild acid conditions to give the racemic glycosal acceptor 7 as is described in Example 7 and shown in FIG. 4.

In preferred embodiments of the invention, the racemic glycosal acceptor 7 has both the 5 and 6-hydroxyl groups exposed. Therefore, reaction of the racemic glycosal acceptor 7 with a glycosyl donor 2 is expected to provide both the 4,5 and 4,6 substituted aminoglycoside analogs.

Figure 5:
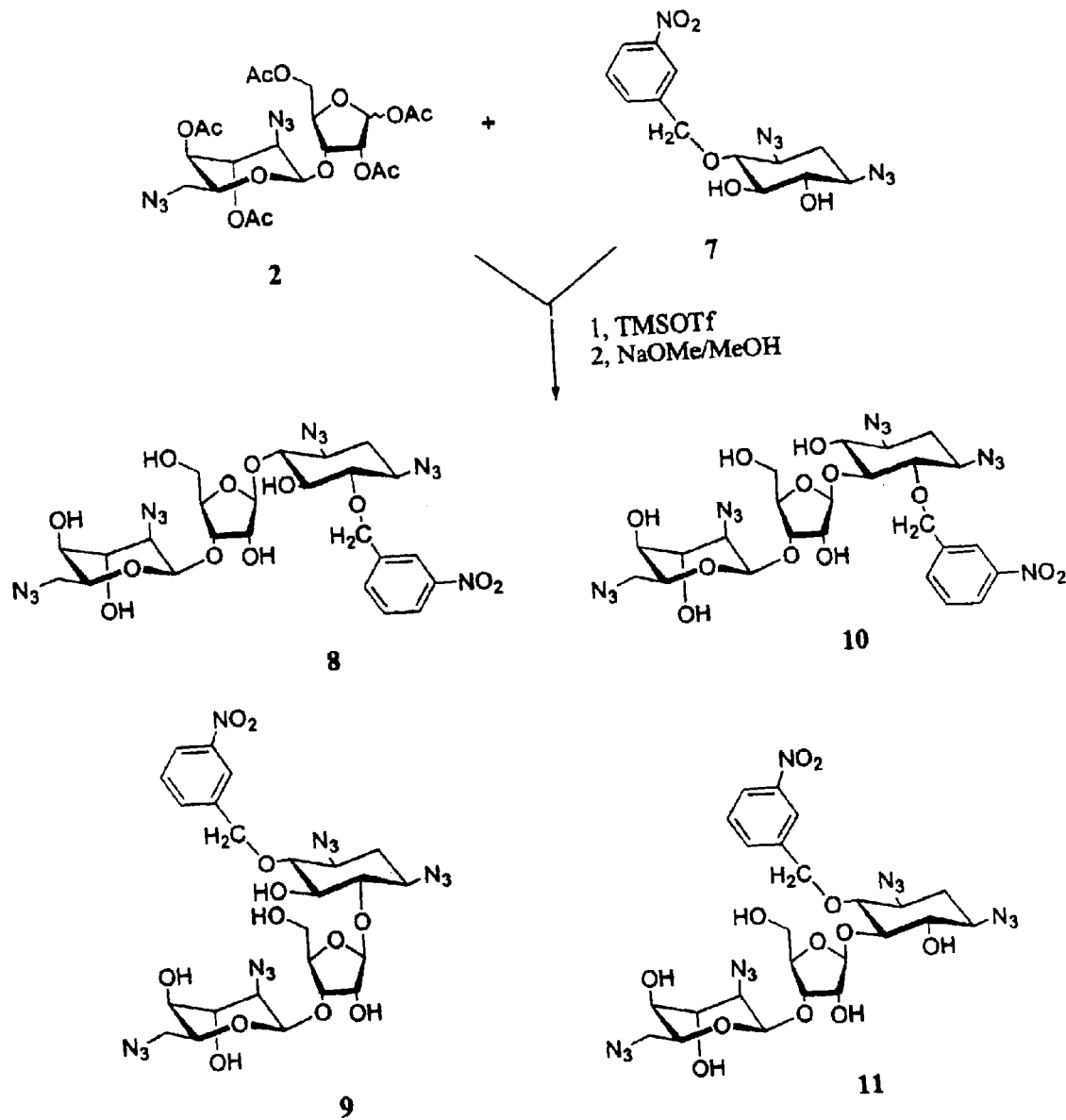
FIG. 5 is a schematic representation of the glycosylation of a glycosyl acceptor with a glycosyl donor.
Figure 6:
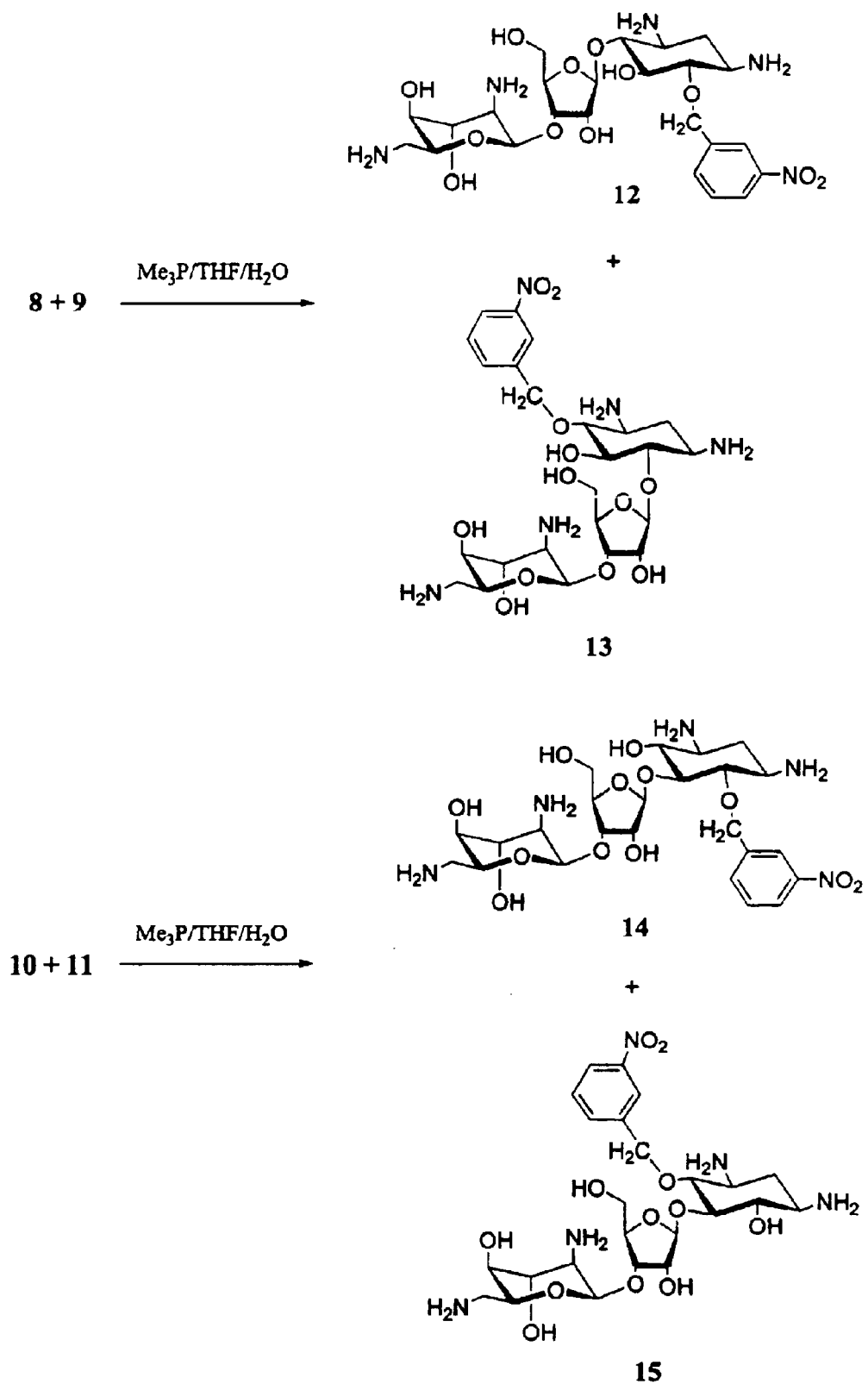
FIG. 6 is a schematic representation of the reduction of azide groups to amino for an aminoglycoside compound of the invention.

In a preferred embodiment of the invention, glycosylation of 7 with 2 under standard conditions, followed by deprotection of the acetyl groups with base, provides a good yield of a mixture of compounds 8–11 as is described in Example 8 and shown in FIG. 5. The 4,6-substituted compounds 8 and 9 are present as the major products, as the 5-hydroxyl group of 7 is fairly hindered. Compounds 8 and 9 are separable from 10 and 11 by silica gel chromatography. In the final deprotection step, the mixtures 8+9 and 10+11 are subjected to treatment with trimethylphosphine to effect the reduction of the azides to the corresponding amines as is described in Example 9 and 10 and shown in FIG. 6. These procedures give the 4,5-substituted paromomycin analogs 12+13 and the 4,6-substituted tobramycin-paromomycin hybrids 14+15, respectively. The mixtures 12+13 and 14+15 may be resolved using standard separation techniques such as chiral HPLC.

In accordance with a aspect of the invention, there is provided a process for making a compound according to formula (I) wherein one of $R_4$ or $R_5$ is the group of formula (II), the process comprising:

partially hydrolyzing a compound of the formula (VI),

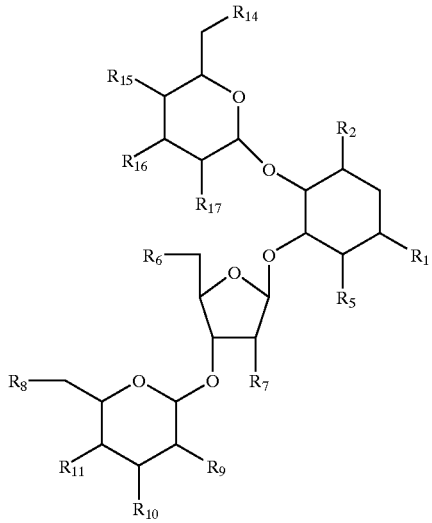

(VI)

to give an intermediate of formula (V)

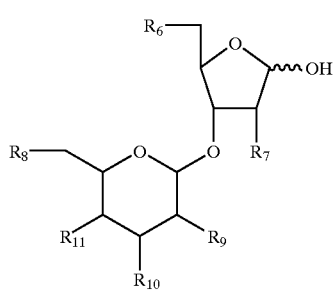

(V)

wherein
$R_1$ and $R_2$ are independently amino or protected amino;
$R_5$, $R_6$ and $R_7$ are independently hydroxyl or protected hydroxyl;
$R_8$, $R_9$, $R_{10}$, $R_{11}$, $R_{14}$, $R_{15}$, $R_{16}$ and $R_{17}$ are independently hydroxyl, protected hydroxyl, amino or protected amino;

converting the anomeric hydroxyl group in formula (V) to a leaving group, thereby providing an activated derivative; and coupling the activated derivative with intermediate (VII)

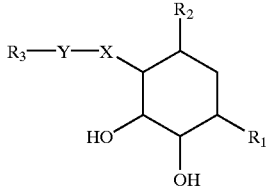

(VII)

to give a compound of formula (VIII) or (IX)

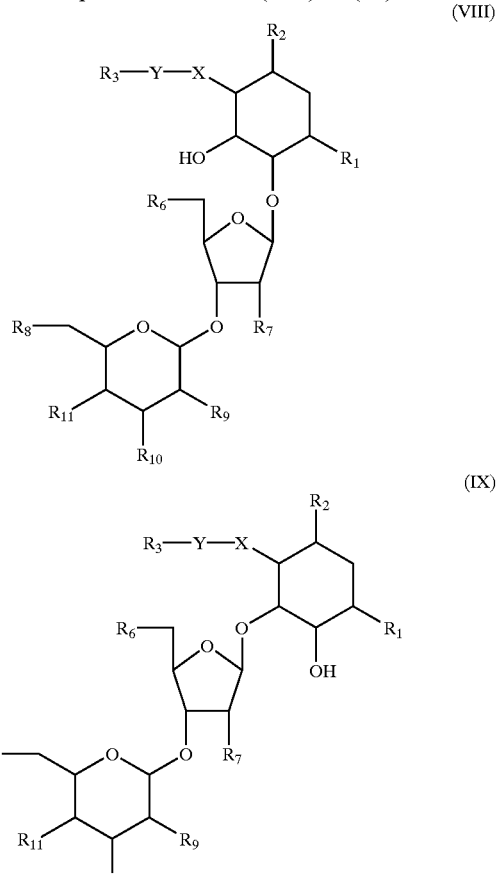

wherein,
X is O, S, NH or $CH_2$;
Y is a bond or a divalent linking group;
$R_3$ is aryl, heteroaryl, substituted aryl or substituted heteroaryl.

In a preferred embodiment, the compound of formula (VIII) is isolated from a mixture of compounds (VIII) and (IX), for example by silica gel chromatography. In a preferred embodiment, the compound of formula (VI) is neomycin B.

The hydroxyl group at the anomeric carbon of furanose ring of intermediate (V) is converted to a suitable leaving group for the coupling step with the protected 2-DOS intermediate (VII). Preferred leaving groups include halogen (Cl or Br) and acetyl (Ac). Alternatively, the leaving group may be a thio leaving group such as SR wherein R may be alkyl e.g. methyl or ethyl, or aryl such as phenyl or p-methylphenyl.

Included within the scope of the present invention are the pharmaceutically acceptable salts of the foregoing compounds. As used herein, the term "pharmaceutically acceptable salts" refers to non-toxic acid addition salts and alkaline earth metal salts of the compounds of the invention. The salts can be prepared in situ during the final isolation and purification of the compounds of the invention, or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali or alkaline earth metal salts include the sodium, calcium, potassium and magnesium salts.

In another aspect of the invention, there is provided a method of treating or preventing a microbial infection in a mammal comprising administering to said mammal an effective amount of a compound according to the invention.

It has been found that the compounds of the present invention possess antibacterial activity against a wide spectrum of gram positive and gram negative bacteria, as well as enterobacteria and anaerobes. The compounds of the invention are therefore useful in the antibiotic treatment of susceptible bacterial infections in both humans and animals. In addition, the compounds, by reason of their in vitro activity, may be used in scrub solutions for surface inhibition of bacterial growth e.g. in sterilization of glasswear or as an additive in fabric laundering compositions.

Susceptible organisms generally include those gram positive and gram negative, aerobic and anaerobic organisms whose growth can be inhibited by the compounds of the invention such as *Staphylococcus, Lactobacillus, Streptococcus, Sarcina, Escherichia, Enterobacter, Klebsiella, Pseudomonas, Acinetobacter, Proteus, Campylobacter, Citrobacter, Nisseria, Baccillus, Bacteroides, Peptococcus, Clostridium, Salmonella, Shigella, Serratia, Haemophilus, Brucella* and other organisms. The compounds of the invention are particularly useful for treating microbial infections such as *K. pneumoniae, E. coli, s. aureus, E. faecalis* and *M. tuberculosis*.

Accordingly there is provided a method of treating bacterial infection in a mammal comprising administering to the mammal, for example a human, an effective amount of a compound of the invention. By "effective amount" is meant an amount of compound which upon administration is capable of reducing or preventing proliferation of the bacteria or reducing or preventing symptoms associated with the bacterial infection. The actual amount of compound administered and the route of administration will depend upon the particular disease or bacteria as well as other factors such as the size, age, sex and ethnic origin of the individual being treated and is determined by routine analysis. The compounds of the invention may also be formulated into compositions together with pharmaceutically acceptable carriers for parenteral injection, for oral administration in solid or liquid form, for rectal administration, and the like. In methods of the invention, the compound may be administered orally (including buccal, sublingual, inhalation), nasally, rectally, vaginally, intravenously, intradermally, subcutaneously and topically. Compounds will be formulated into compositions suitable for administration for example with suitable carriers, diluents, thickeners, adjuvants, etc. As are routine in the formulation art. Compositions of the invention may also include additional active ingredients. Dosage forms include solutions, powders, tables, capsules, gel capsules, suppositories, topical ointments and creams and aerosols for inhalation.

Formulations for non-parenteral administration may include sterile aqueous solutions which may also contain buffers, diluents and other suitable additives. Pharmaceutically acceptable organic or inorganic carrier substances suitable for non-parenteral administration which do not deleteriously react with compounds of the invention can be used. Suitable pharmaceutically acceptable carries include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like. The formulations can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously react with compounds of the invention. Aqueous suspensions may contain substances which increase the viscosity of the suspension including, for example, sodium carboxymethylcellulose, sorbitol and/or dextran. Optionally, the suspension may also contain stabilizers.

In a preferred embodiment, compounds of the invention are administered via oral delivery. Compositions for oral administration include powders or granules, suspensions or solutions in water or non-aqueous media, capsules, sachets, troches, tablets or SECs (soft elastic capsules or caplets). Thickeners, flavoring agents, diluents, emulsifiers, dispersing aids, carrier substances of binders may be desirably added to such formulations. The use of such formulations has the effect of delivering the nucleic acid to the alimentary canal for exposure to the mucosa thereof. Accordingly, the formulation can consist of material effective in protecting the compound from pH extremes of the stomach, or in releasing the compound over time, to optimize the delivery thereof to a particular mucosal site. Enteric coatings for acid-resistant tablets, capsules and caplets are known in the art and typically include acetate phthalate, propylene glycol and sorbitan monoleate.

Various methods for producing formulations for alimentary delivery are well known in the art. See, generally, Nairn, Chapter 83; Block, Chapter 87; Rudnic et.al., Chapter 89; and Longer et.al., Chapter 91 In: Remington's Pharmaceutical Sciences, 18$^{th}$ Ed., Gennaro, ed., Mack Publishing Co., Easton, Pa., 1990. The formulations of the invention can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present in a concentration of about 0.5% to about 95% by weight of the total mixture, that is to say in amounts which are sufficient to achieve the desired dosage range. The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

Compositions may be formulated in a conventional manner using additional pharmaceutically acceptable carriers or excipients as appropriate. Thus, the composition may be prepared by conventional means with additional carriers or excipients such as binding agents (e.g., pregelatinised maize starch, polyvinylpyrrolidone or hydroxypropyl methylcellulose); filters (e.g., lactose, microcrystalline cellulose or calcium hydrogen phosphate); lubricants (e.g., magnesium stearate, talc or silica); disintegrates (e.g., starch or sodium starch glycolate); or wetting agents (e.g., sodium lauryl sulfate). Tablets may be coated by methods will known in the art. The preparations may be also contain flavoring, coloring and/or sweetening agents as appropriate.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided soled carriers or both, and then, if necessary, shaping the product.

Formulations of the present invention suitable for oral administration may be presented as discrete units such as capsules, cachets or tables each containing predetermined amounts of the active ingredients; as powders or granules; as solutions or suspensions in an aqueous liquid or a non-aqueous liquid; or as oil-in-water emulsions or water-in-oil liquid emulsions. A tablet may be made by compression or molding, optionally with one or more accessory ingredients. Compressed tablets may be prepared by compressing in a suitable machine, the active ingredients in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredients therein.

EXAMPLES

General

NMR spectra were obtained with the following instruments: $^1$H NMR: Varian Gemini-200 (199.975 MHZ) or Varian Unity 400 (399.952 MHZ). $^{13}$C NMR: Varian Gemini-200 (50.289 MHZ). $^{31}$P NMR: Varian Gemini-200 (79.990 MHZ). NMR spectra were recorded using either deuteriochloroform, dimethylsulfoxide-$d_6$ (DMSO), dimethylformamide-$d_7$, or deuteriomethanol as solvent (tetramethylsilane as internal standard). The following abbreviations are used to designate the multiplicity of individual signals: s=singlet, d=doublet, t=triplet, q=quartet, m=multiplet, dd=doublet of doublets, ddd=doublet of doublet of doublets, br s=broad singlet. Mass spectra were acquired on an HP MSD 1100 mass spectrometer.

Example 1

Neobiosamine Hydrochloride (1)

A solution of neomycin sulfate (20.0 g, 20.8 mmol) in methanol (50 mL) is brought to a boil, to which concentrated HCl (18 g, 12.1 N) is added dropwise. The solution is refluxed for 6 hours before all the reactants are completely consumed. The reaction solution is cooled to room temperature, evaporated to half of its volume, and cooled to 0° C. The solid precipitate is removed by filtration. Further evaporation of the solvent gives the desired product 1 as a syrup (8 g). The product is used directly in the next step without purification.

Example 2

Per-O-Acetyl-Diazido-Neobiosamine (2)

Triflic azide solution (Warning: TfN$_3$ has been reported to be explosive when not in solvent and should always be used as a solution (Caveander, C. J.; Shiner, V. J., *J. Org. Chem.*, 1981, 46, 5173)) (ca. 0.5 M in dichloromethane, 80 mL, 40 mmol) is added slowly by drop wise addition to a mixture of neobiosamine hydrochloride 1 (5.0 g, 11.9 mmol), potassium carbonate (4 g, 28 mmol), and CuSO$_4$ (200 mg, 1.21 mmol) in H$_2$O (30 mL). Methanol (200 mL) is added to give a homogenous solution. The reaction is allowed to stir for 18 hours at room temperature and is concentrated under reduced pressure. The residue is dissolved in anhydrous pyridine (50 mL), cooled to 0° C., and acetic anhydride (30 mL) is added. After stirring for 12 hours at room temperature, the solution is co-evaporated with toluene (2×50 mL) and the resulting residue is purified on a silica gel column using hexane-ethyl acetate (1:1) to give per-O-acetyl-diazido-neobiosamine 2 as a colorless oil (4 g, 58.5%). $^{13}$C NMR (CDCl$_3$, 400 MHZ): d 98.5, 98.1, 97.2, 74.0, 69.4, 68.6, 68.6, 66.7, 66.2, 61.2, 57.1, 57.2.

Example 3

2-Deoxystreptamine Hydrobromide (3)

A solution of neomycin sulfate (20 g, 20.8 mmol) in HBr (150 mL, 48%) is stirred under reflux at 100° C. for 40 hours. The solution is concentrated to dryness at 60° C. under reduced pressure. The residue is dissolved into water (H$_2$O) (100 mL), and activated charcoal (10 g) is added. After stirring at room temperature for 10 hours, the charcoal is removed by filtration through Celite, and the solution is concentrated to a syrup. Methanol (100 mL) is added and the mixture is stirred for 2 hours t room temperature. The solid product is filtered to give 2-deoxystreptamine hydrobromide 3 (4.1 g, 61%). R$_f$: 0.2 (CH$_3$OH/NH$_4$OH=4:1); $^1$H-NMR (D$_2$O, 200 MHZ): d 1.95 (1H, ddd), 2.5 (1H, m), 3.2–3.6 (9H, m); $^{13}$C-NMR (D$_2$O, 200 MHZ): d 40.0, 65.0, 87.2, 89.5.

Ref. Georgiadas, M. P.; Constantinou-Kokotou, V. *J. Carbohydr. Chem.* 1991, 10, 739–746.

Example 4

2-Deoxy-1,3-Diazidostreptamine (4)

To a solution of 2-deoxy-1,3-diazidostreptamine 4 (1.6 g, 5 mmol), sodium azide (NaN$_3$) (23.4 g, 350 mmol), and potassium carbonate (K$_2$CO$_3$) (7 g, 35 mmol) in of H$_2$O (50 mL) is added dichloromethane (CH$_2$Cl$_2$) (25 mL) and trifluoroacetic anhydride (Tf$_2$O) (5 g, 25 mmol) at 0° C. After stirring for 2 hours, CuSO$_4$ (30 mg) is added. The mixture is stirred at room temperature for 22 hours. A major product is observed by t.l.c. (CH$_2$Cl$_2$—CH$_3$COCH$_3$=1:1). 1 N sodium hydroxide (NaOH) is added to give a homogenous solution. The solution is extracted with ethyl acetate (EtOAc) (5×50 mL). The organic extracts are combined, evaporated and the residue is purified on a silica gel column using dichloromethane-acetone (CH$_2$Cl$_2$—CH$_3$COCH$_3$) (1:1). The fractions are combined and evaporated to give, 2-Deoxy-1,3-diazidostreptamine 4 as a colorless oil (0.850 g, 68%). $^1$H NMR (200 MHZ, CD$_3$OD): d 3.35 (m, 5H), 2.20 (ddd, 1H), 1.38 (ddd, 1H); $^{13}$C NMR (200, CD$_3$OD): d 77.7, 76.9, 62.3, 33.4.

Ref. Alper, P. B.; Hung, S. C.; Wong, C. H. *Tetrahedron Lett.* 1996, 37, 6029–6032.

Example 5

Racemic 2-Deoxy-1,3-Diazido-4,5-O-Isopropylidene-Streptamine (5)

To a solution of 2-deoxy-1,3-diazidostreptamine 4 (0.890 g, 4.2 mmol) in dry dimethoxypropane (25 mL) is added p-toluenesulfonic acid (20 mg). After stirring at room temperature for 12 hours, triethylamine (0.1 mL) is added to quench the reaction. The solvent is evaporated, and the residue is purified on a silica gel column using hexaneethyl acetate (4:1) to give the desired product 2-deoxy-1,3-diazido-4,5-O-isopropylidinestreptamine 5 (0.770 g, 70%) as white solid. $^{13}$C NMR (CDCl$_3$, 200 MHZ): d 112.7, 79.5, 74.7, 74.0, 62.5, 57.2, 32.0, 26.7, 27.8.

Example 6

(±)-2-Deoxy-1,3-Diazido4,5-O-Isopropylidine6-O-(3-Nitrobenzyl)-Streptamine (6)

To a solution of 2-deoxy-1,3-diazido-4,5-O-isopropylidine-streptamine 5 (0.500 g, 1.97 mmol) in dry N,N-dimethylformamide (DMF) (10 mL) is added NaH (120 mg, 60% dispersion in mineral oil) at 0° C. After stirring for 10 min under argon, 3-nitrobenzylbromide (0.860 g, 4.0 mmol) is added and the mixture is stirred for 12 hours at room temperature. The excess NaH is quenched by the addition of methanol (1 mL), and DMF is removed on a rotary evaporator. The resulting residue is purified on a silica gel column using hexane/ethyl acetate (4:1) to give 0.510 g (66.6%) of (±)-2-deoxy-1,3-diazido-4,5-O-isopropylidine-6-O-(3-nitrobenzyl)-streptamine 6 as white solid. $^1$H NMR (200 MHZ, CDCl$_3$): d 4.87 (q, 2H), 4.05 (dd, 1H), 3.50 (m, 4H), 2.2 (m, 1H), 2.10 (s, 3H), 1.95 (s, 3H), 1.35 (m, 1H); $^{13}$C NMR (200 MHZ, CDCl$_3$): d 112.3, 81.3, 80.0, 79.5, 71.5, 61.0, 57.2, 34.0, 26.4, 26.3.

Example 7

(±)-2-Deoxy-1,3-Diazido-6-O-(3-Nitrobenzyl)-Streptamine (7)

A solution of (±)-2-deoxy-1,3-diazido-4,5-O-isopropylidine-6-O-(3-nitrobenzyl)-streptamine 6 (0.300 g, 0.77 mmol) in acetic acid (aq) (80%, 20 mL) is kept for 2 hours at 75° C. A major product is observed by t.l.c (hexane-ethyl acetate, 2:1). Toluene is added to co-evaporate the solvents. Purification of the residue on a silica gel column using hexane-ethyl acetate (2:1) gave (±)-2-deoxy-1,3-diazido-6-O-(3-nitrobenzyl)-streptamine 7 (0.150 g, 55.8%) as white solid. $^{13}$C NMR (CDCl$_3$, 200 MHZ): d 84.0, 76.2, 75.8, 73.8, 60.1, 58.3, 32.1.

Example 7

2-Deoxy-1,3-Diazido-6-O-(3-Nitrobenzyl)-4-O-[3-O-(2,6-Diazido-2,6-Dideoxy-b-L-Idopyranosyl)-b-D-Ribofuranosyl]-Streptamine (8), 2-Deoxy-1,3-Diazido-4-O-(3-Nitrobenzyl)-6-O-[3-O-(2,6-Diazido-2,6-Dideoxy-b-L-Idopyranosyl)-b-D-Ribofuranosyl]-Streptamine (9), 2-Deoxy-1,3-Diazido-6-O-(3-Nitrobenzyl)-5-O-[3-O-(2,6-Diazido-2,6-Dideoxy-b-L-Idopyranosyl)-b-D-Ribofuranosyl]-Streptamine (10), and 2-Deoxy-1,3-Diazido-4-O-(3-Nitrobenzyl)-5-O-[3-O-(2,6-Diazido-2,6-Dideoxy-b-L-Idopyranosyl)-b-D-Ribofuranosyl]-Streptamine (11)

To a solution of (±)-2-deoxy-1,3-diazido-6-O-(3-nitrobenzyl)-streptamine 7 (0.150 g, 0.43 mmol) and per-O-acetyl-diazido-neobiosamine 2 (0.300 g, 0.5 mmol) in dry dichloromethane (3 mL) is added 4 Å molecular sieve (0.500 g) under N$_2$. After stirring at room temperature for 2 hours, trimethylsilyl trifluoromethanesulfonate (TMSOTf) (100 μL, 0.45 mmol) is added to the solution, and the reaction is stirred for another 10 hours at room temperature. Triethylamine (0.5 mL) is added, and the solution is filtered, and concentrated to dryness. The residue is purified on a silica gel column using hexane-ethyl acetate (1:1) to give the coupled products (0.170 g). This mixture is dissolved in dry methanol (5 mL) and a solution of sodium methoxide (NaOMe) (1 N in methanol) (0.3 mL) is added. The solution is stirred for 30 min at room temperature. After neutralization with H$^+$ resin, the solution is filtered and concentrated to dryness. The residue is purified on a silica gel column using dichloromethane-methanol (CH$_2$Cl$_2$—MeOH) (10:1) to give compounds 8 and 9 as a mixture in a 1:1 ratio (90 mg), and compounds 10 and 11 as a mixture in a 1:1 ratio (20 mg). Spectral data for compounds 8 and 9: $^1$H NMR (400 MHZ, CDCl$_3$): d 5.18 (d, 1H, J<1.0 Hz), 5.15 (d, 1H, J=13.2 Hz), 5.02 (d, 1H, J<1.0 Hz), 4.98 (s, 2H), 4.88 (d, 1H, J=13.2 Hz), 4.82 (d, 1H, J=4.4 Hz), 4.71 (d, 1H, J=6.2 Hz), 2.20 (m, 2H), 1.14 (m, 2H); $^{13}$H NMR (400 MHZ, CDCl$_3$): d 102.5, 102.1, 99.8, 99.2, 87.1, 85.6, 84.0, 83.0, 79.8, 75.3, 75.3, 75.2, 74.4, 73.9, 70.4, 70.1 69.3, 69.2, 69.0, 68.8, 67.1, 66.5, 64.7, 64.6, 61.2, 61.1, 60.6, 59.9, 59.5, 59.2, 51.2, 51.2, 50.8, 50.8, 32.1, 32.0; MS: m/z 716 [M+Na]$^+$. Spectral data for compounds 10 and 11: $^1$H NMR (400 MHZ, CDCl$_3$): d 5.20 (d, 1H, J<1 Hz), 5.14 (d, 1H, J<1 Hz), 5.06 (d, 1H, J=4.2 Hz), 5.05 (d, 1H, J=12.2 Hz), 4.97 (q, 2 H), 4.91 (d, 1H, J=6.2 Hz), 4.83 (d, 1H, J=12.2 Hz), 2.25 (m, 2H), 1.42 (m, 2H); MS: m/z 716 [M+Na]$^+$.

Example 8

2-Deoxy-6-O-(3-Nitrobenzyl)-4-O-[3-O-(2,6-Diamino-2,6-Dideoxy-b-L-Idopyranosyl)-b-D-Ribofuranosyl]-Streptamine (12), and 2-Deoxy-4-O-(3-Nitrobenzyl)-6-O-[3-O-(2,6-Diamino-2,6-Dideoxy-b-L-Idopyranosyl)-b-D-Ribofuranosyl]-Streptamine (13)

The mixture of compounds 8 and 9 (28 mg, 1:1,) is dissolved in tetrahydrofuran (THF) (5 mL) and water (H$_2$O) (0.5 mL) and 1 N sodium hydroxide (NaOH) (0.5 mL) are added. A solution of trimethylphospine (PMe$_3$) in THF (1 N, 0.5 mL) is added, and the reaction is allowed to stir for 10 hours at room temperature. The solvent is evaporated, and the residue is purified by loading it onto a silica gel column and eluting the products with a gradient of 0%, 2.5% and 25% concentrated ammonia (NH$_3$) in methanol (MeOH). The product fractions are collected and co-evaporated with toluene (3×10 mL). After lyophilization, neutralization, and re-lyophilization, 25 mg (84%) of compounds 12 and 13 are obtained as a mixture in a 1:1 ratio. $^1$H NMR (D$_2$O, 400 MHz): d 5.35 (d, 1H, J<1 Hz), 5.08 (d, 1H J=12.5 Hz), 5.07 (d, 1H, J<1 Hz), 5.00 (d, 1H, J=13.0 Hz), 4.90 (d, 1H, J=4.2 Hz), 4.86 (d, 1H, J=12.5 Hz), 4.83 (d, 1H, J=13.0 Hz), 4.82 (d, 1H, J=6.2 Hz), 2.4 (m, 2H), 1.8 (m, 2H); MS: m/z 590 [M+H]$^+$.

Example 8

2-Deoxy-6-O-(3-Nitrobenzyl)-5-O-[3-O-(2,6-Diamino-2,6-Dideoxy-b-L-Idopyranosyl)-b-D-Ribofuranosyl]-Streptamine (14), and 2-Deoxy-4-O-(3-Nitrobenzyl)-5-O-[3-O-(2,6-Diamino-2,6-Dideoxy-b-L-Idopyranosyl)-b-D-Ribofuranosyl]-Streptamine (15)

The deprotection of the mixture of compounds 10 and 11 (9 mg, 1:1) is accomplished as per the procedure in Example 7. The procedure gives 5.5 mg (53 %) of compounds 14 and 15 as a mixture in a 1:1 ratio. $^1$H NMR (D$_2$O, 400 MHz): d 5.33 (s, 1H), 5.30 (s, 1H), 5.0 (d, 1H, J=4.2 Hz), 4.97 (d, 1H, J=12 Hz), 4.86 (d, 1H, J=12 Hz), 4.79 (d, 1H, J=5.2 Hz), 4.77 (s, 2H), 2.38 (m, 2H), 1.75 (m, 2H); MS: m/z 590 [M+H]$^+$.

Example 9

Glycoside Coupling With Thio Leaving Group

Figure 7:
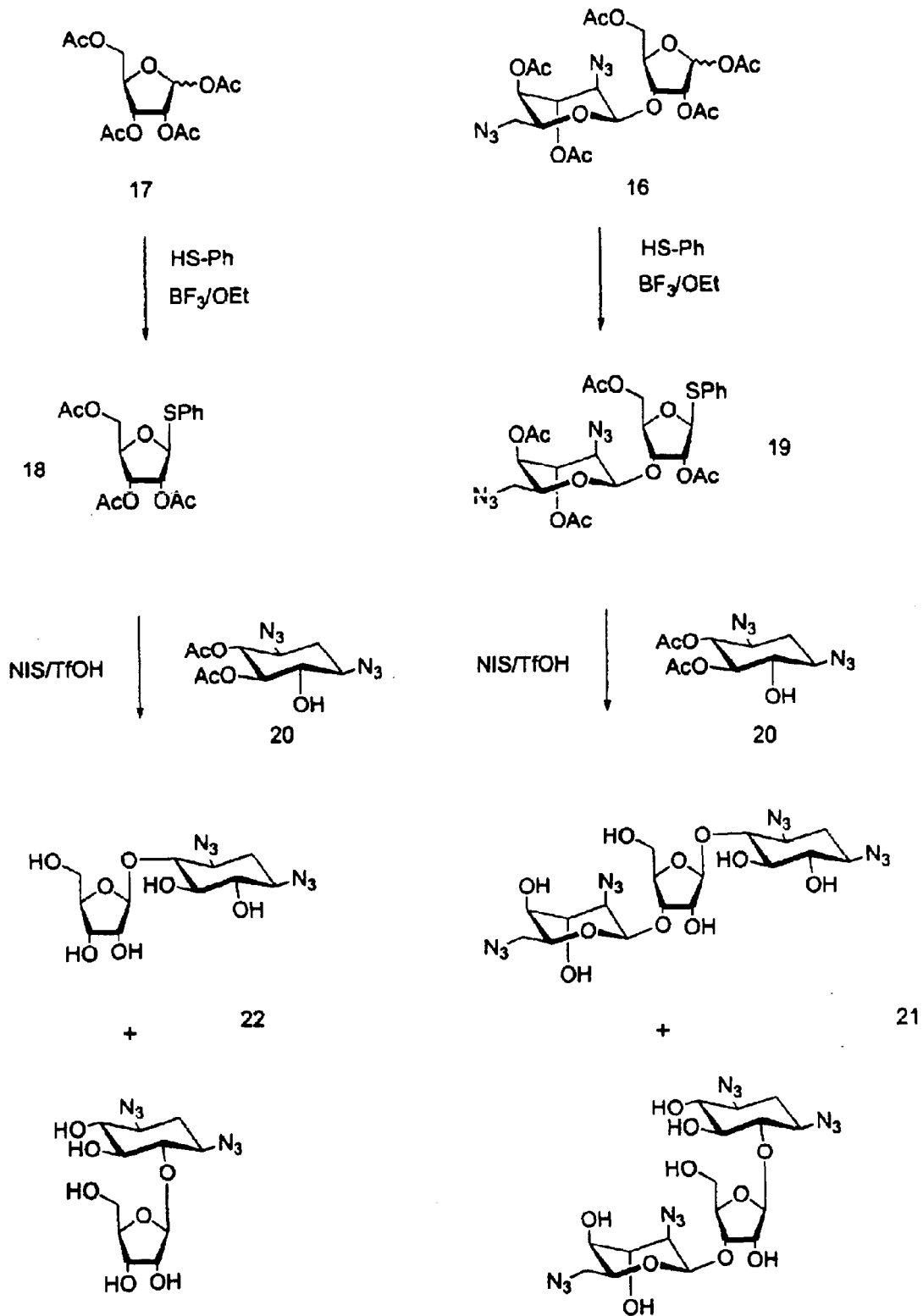
FIG. 7 is a schematic representation of glycosylation of 2-DOS with a thioglycosyl donor.

Referring to FIG. 7, per-O-acetyl-diazido-neobiosamine (16) and per-O-acetyl ribofuranose (17) were used as the starting materials. Treatment of 17 with 3 equiv. of thiophenol in the presence of BF$_3$/OEt (1.5 equiv.) in CH$_2$Cl$_2$ gave the per-O-acetyl phenyl 1-thio beta D-ribofuranoside (18) in high yield. Using the same procedure, compound 16 was transferred into its corresponding 1-thio glycoside donor 19 in 70% yield.

Compounds 18 and 19 were used to couple with racemic acceptor 2-deoxy-1,3-diazido-4,5-di-O-acetyl-streptamine (20) in the presence of NIS/TfOH, and both reactions gave the coupling products 21 and 22 in more than 50% yields.

Example 10

In Vitro Antibacterial Activity Determination of Minimum Inhibitory Concentrations (MICs).

The assays are carried out in 150 μL volume in duplicate in 96-well clear flat-bottom plates. The bacterial suspension from an overnight culture growth in appropriate medium is added to a solution of test compound in 4% DMSO in water. Final bacterial inoculum is approximately 10$^5$–10$^6$ CFU/well. The percent growth of the bacteria in test wells relative to that observed for a well containing no compound is determined by measuring absorbance at 595 nm (A$_{595}$) after 24 h. The MIC is determined as a range of single compound where the complete inhibition of growth is observed at the higher concentration and cells are viable at the lower concentrations. Both ampicillin and tetracycline are used as antibiotic-positive controls in each screening assay for *S. pyogenes, E. coli* imp-, *E. coli, S. aureus, E. faecalis, K. pneumoniae* and *P. vulgaris*. Ciprofloxacin is used as an antibiotic positive control in each screening assay for *P. aeruginosa*.

Example 11

Animal and In Vivo studies.

Male ICR mice are fed with autoclaved commercial food pellets and sterile water ad libitum. Animals are inoculated intraperitoneally with 8.0×10$^6$ CFU/0.5 mL/mouse of *K. pneumoniae* (ATCC 10031) in BHI containing 5% mucin. Ten animals each are randomly assigned to either control or treatment groups. Test compound and gentamycin (included as a positive control) are both administered subcutaneously one hour after infection. Test compound is administered as a solution in DMSO (100%) and 50 μL/mouse. Gentamycin is administered as an aqueous buffer solution (phosphate buffered saline (PBS), pH=7.4).

Example 12

Coupled Bacterial Transcription/Translation Assay.

The DNA template, pBestLuc™ (Promega), is a plasmid containing a reporter gene for firefly luciferase fused to a strong tac promoter and ribosome binding site. Messenger RNA from 1 μg pBestLuc is transcribed and translated in *E. coli* S30 bacterial extract in the presence or absence of test compound. Compounds are tested in a black 96 well microtiter plate with an assay volume of 35 μL. Each test well contains: 5 μL test compound, 13 μL S30 premix (Promega), 4 μL 10X complete amino acid mix (1 mM each), 5 μL *E. coli* S30 extract and 8 μL of 0.125 μg/μL pBestLuc™. The transcription/translation reaction is incubated for 35 minutes at 37° C. followed by detection of functional luciferase with the addition of 30 μL LucLite™ (Packard). Light output is quantitated on a Packard TopCount.

Example 13

Amino Acid Misincorporation Assay.

A mutant form of ubiquitin devoid of the amino acid tyrosine is produced in vitro in *E. coli* S-30 extracts in the presence of a tritiated tyrosine. Since ubiquitin has no tyrosine in the sequence, if tyrosine is used as the labeled amino acid, any incorporated counts above background are assumed to be due to the misincorporation of the tritiated amino acid. The labeled protein is captured via a ubiquitin antibody which is associated with anti-rabbit SPA beads. Altered ubiquitin molecules are not efficiently captured by the antibody. Compounds are tested in 96 well microtiter plate in an assay volume of 10 μL. Control experiments using the antibiotics, kanamycin, novabiocin, monensin, gentamicin, neomycin, tetracycline are run at 5 μM of each antibiotics.

TABLE 1

| Compound | Assay | inhibition (%) | concentration (μM) |
|---|---|---|---|
| 12 + 13 | transc/transl | 0 | ≦100 μM |
|  | *E. coli* (imp) | 56 | ≦500 |
|  | *S. pyogenes* | 99 | ≦125 |
| 14 + 15 | transc/transl | 96 | ≦100 |
|  | *E. coli* (imp) | 95 | ≦500 |
|  | *S. pyogenes* | 99 | ≦125 |

What is claimed is:
1. A compound of formula I:

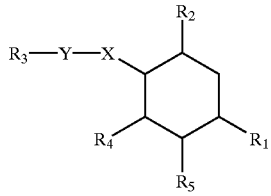

(I)

wherein
  R$_1$ and R$_2$ are independently amino or protected amino;
  X is O, S, NH or CH$_2$;
  Y is (CH$_2$)$_n$;
  n is 1 to 10;
  R$_3$ is aryl or heteroaryl;
  or R$_3$ is a substituted aryl or a substituted heteroaryl having at least one substituent group selected from the list consisting of OH, SH, Cl, F, Br, I, CN, NH$_2$, NO$_2$, amidine, guanidine, COOH, C$_{1-8}$ alkyl, C$_{2-8}$ alkenyl, alkynyl, CF$_3$, OCF$_3$, saturated or unsaturated carbocycle, saturated or unsaturated heterocycle, aryl, heteroaryl, OR$_{14}$, SR$_{14}$, NHR$_{14}$, N(R$_{14}$)$_2$, C(S)R$_{14}$, C(O)R$_{14}$, C(O)NHR$_{14}$, C(O)OR$_{14}$, OC(O)R$_{14}$, wherein R$_{14}$ is hydrogen, C$_{1-8}$ alkyl, C$_{2-8}$ alkenyl, C$_{2-8}$ alkynyl, carbocyclic, heterocyclic, aryl or a heteroaryl group;
  one of R$_4$ and R$_5$ is hydroxyl or protected hydroxyl, and the other is selected from the group consisting of formula II and IV:

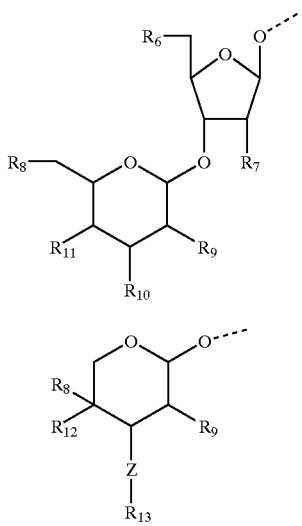

(II)

(IV)

wherein
R$_6$ and R$_7$ are independently hydroxyl or protected hydroxyl;
R$_8$, R$_9$, R$_{10}$, and R$_{11}$ are independently hydroxyl, protected hydroxyl, amino or protected amino;
R$_{12}$ and R$_{13}$ are independently H or alkyl; and
Z is O, S or NH.

2. The compound of claim 1, wherein R$_3$ is selected from the group consisting of phenyl, tolyl, benzyl, naphthyl, anthracyl, phenanthryl, xylyl pyrrole, furan, thiophene, pyrazole, imidazole, triazole, tetrazole, oxazole, oxadiazole, thiazole, thiadiazole, indole, carbazole, benzofuran, benzothiophene, indazole, benzimidazole, benzotriazole, benzoxazole, benzthiazole, benzothiadiazole, purine, pyridine, pyridazine, pyrimidine, pyrazine, triazine, quinoline, acridine, isoquinoline, cinnoline, phthalazine, quinazoline, quinoxaline, phenazine, and phenanthroline.

3. The compound of claim 2, wherein R$_3$ is phenyl.

4. The compound of claim 3, wherein said phenyl group is substituted with Cl, F, OH, NH$_2$, CN, NO$_2$, CF$_3$ or alkoxy.

5. The compound of claim 1, wherein X is O.

6. The compound of claim 1, wherein Y is methylene.

7. The compound of claim 1, having the formula Ia:

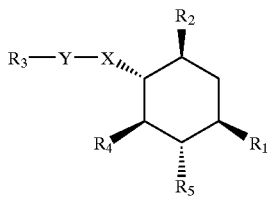

(Ia)

wherein
R$_1$ and R$_2$ are independently amino or protected amino;
X is O, S, NH CH$_2$;
Y is (CH$_2$)$_n$;
n is 1 to 10;
R$_3$ is aryl or heteroaryl;
or R$_3$ is a substituted aryl or a substituted heteroaryl having at least one substituent group selected from the list consisting of OH, SH, Cl, F, Br, I, CN, NH$_2$, NO$_2$, amidine, guanidine, COOH, C$_{1-8}$ alkyl, C$_{2-8}$ alkenyl, alkynyl, CF$_3$, OCF$_3$, saturated or unsaturated carbocycle, saturated or unsaturated heterocycle, aryl, heteroaryl, OR$_{14}$, SR$_{14}$, NHR$_{14}$, N(R$_{14}$)$_2$, C(S)R$_{14}$, C(O)R$_{14}$, C(O)NHR$_{14}$, C(O)OR$_{14}$, OC(O)R$_{14}$, wherein R$_{14}$ is hydrogen, C$_{1-8}$ alkyl, C$_{2-8}$ alkenyl, C$_{2-8}$ alkynyl, carbocyclic, heterocyclic, aryl or a heteroaryl group;
one of R$_4$ and R$_5$ is hydroxyl or protected hydroxyl, and the other is selected from the group consisting of formula II and IV:

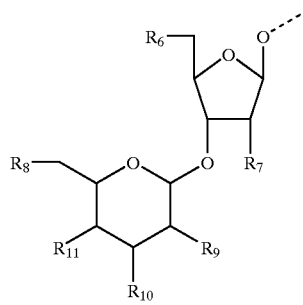

(II)

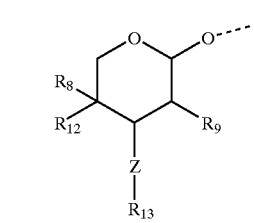

(IV)

wherein
R$_6$ and R$_7$ are independently hydroxyl or protected hydroxyl;
R$_8$, R$_9$, R$_{10}$, and R$_{11}$ are independently hydroxyl, protected hydroxyl, amino or protected amino;
R$_{12}$ and R$_{13}$ are independently H or alkyl; and
Z is O, S or NH.

8. The compound of claim 1 having the formula Ib:

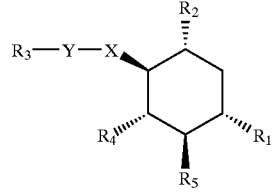

(Ib)

wherein
R$_1$ and R$_2$ are independently amino or protected amino;
X is O, S, NH or CH$_2$;
Y is (CH$_2$)$_n$;
n is 1 to 10;
R$_3$ is aryl or heteroaryl;
or R$_3$ is a substituted aryl or a substituted heteroaryl having at least one substituent group selected from the list consisting of OH, SH, Cl, F, Br, I, CN, NH$_2$, NO$_2$, amidine, guanidine, COOH, C$_{1-8}$ alkyl, C$_{2-8}$ alkenyl, alkynyl, CF$_3$, OCF$_3$, saturated or unsaturated carbocycle, saturated or unsaturated heterocycle, aryl, heteroaryl, OR$_{14}$, SR$_{14}$, NHR$_{14}$, N(R$_{14}$)$_2$, C(S)R$_{14}$, C(O)R$_{14}$C(O)NHR$_{14}$, C(O)OR$_{14}$, OC(O)R$_{14}$, wherein R$_{14}$ is hydrogen, C$_{1-8}$ alkyl, C$_{2-8}$ alkenyl, C$_{2-8}$ alkynyl, carbocyclic, heterocyclic, aryl or a heteroaryl group;
one of R$_4$ and R$_5$ is hydroxyl or protected hydroxyl, and the other is selected from the group consisting of formula II and IV:

(II)

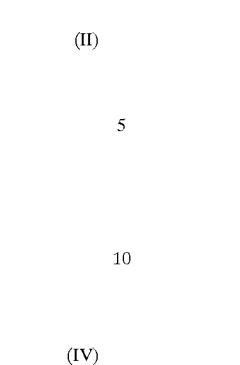

(IV)

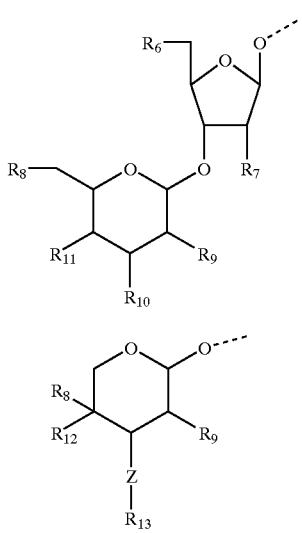

wherein $R_6$ and $R_7$ are independently hydroxyl or protected hydroxyl;

$R_8$, $R_9$, $R_{10}$, and $R_{11}$ are independently hydroxyl, protected hydroxyl, amino or protected amino;

$R_{12}$ and $R_{13}$ are independently H or alkyl; and

Z is O, S or NH.

9. The compound of claim 1 wherein one of $R_4$ or $R_5$ is selected from the group consisting of formulas IIa and IVa:

(IIa)

(IVa)

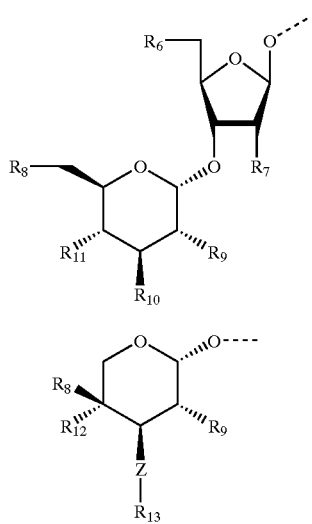

wherein $R_6$ and $R_7$ are independently hydroxyl or protected hydroxyl;

$R_8$, $R_9$, $R_{10}$, and $R_{11}$ are independently hydroxyl, protected hydroxyl, amino or protected amino;

$R_{12}$ and $R_{13}$ are independently H or alkyl; and

Z is O,S or NH.

10. The compound of claim 1, wherein n is 1.

11. The compound of claim 1, wherein one of $R_4$ and $R_5$ is hydroxyl or protected hydroxyl and the other of $R_4$ and $R_5$ is a group of formula II:

(II)

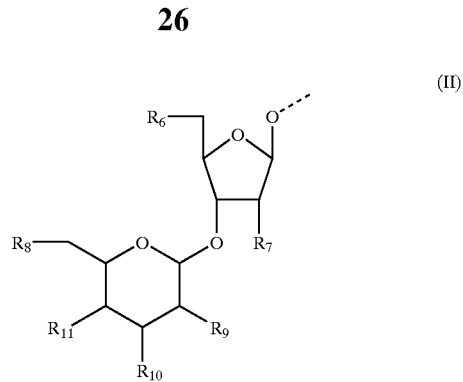

wherein $R_6$ and $R_7$ are each independently hydroxyl or protected hydroxyl; and $R_8$, $R_9$, $R_{10}$, and $R_{11}$ are each independently hydroxyl, protected hydroxyl, amino or protected amino.

12. The compound of claim 11, wherein $R_4$ is hydroxyl or protected hydroxyl and $R_5$ is the group of formula II.

13. The compound of claim 11, wherein $R_8$ and $R_9$ are each independently amino or protected amino and $R_{10}$ and $R_{11}$ are each independently hydroxyl or protected hydroxyl.

14. A process for making the compound of claim 11, comprising: (i) partially hydrolyzing a compound of the formula VI, (VI)

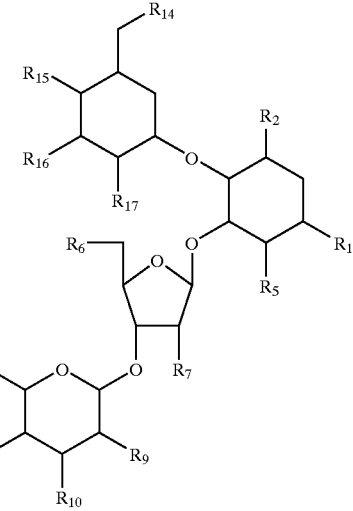

to provide an intermediate of formula V, (V)

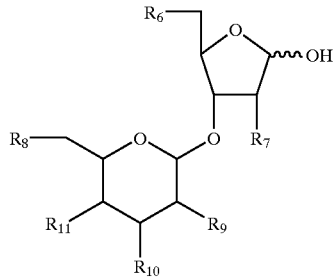

wherein $R_1$ and $R_2$ are independently amino or protected amino;

$R_5$, $R_6$ and $R_7$ are independently hydroxyl or protected hydroxyl;

$R_8, R_9, R_{10}, R_{11}, R_{14}, R_{15}, R_{16}$ and $R_{17}$ are independently hydroxyl, protected hydroxyl, amino or protected amino;

(ii) converting the anomeric hydroxyl in said intermediate of formula (V) to a leaving group, thereby producing an activated compound; and (iii) coupling said activated compound with intermediate VII,

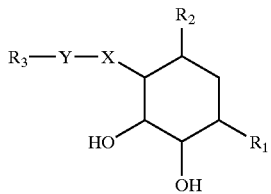
(VII)

to give a compound of formula VIII or IX,

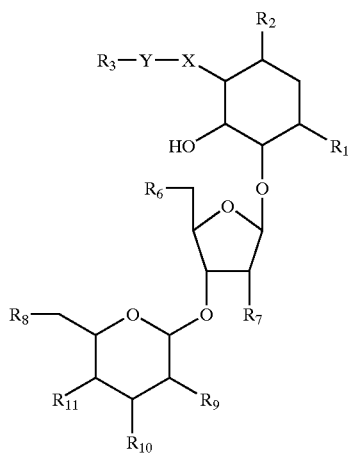
(VIII)

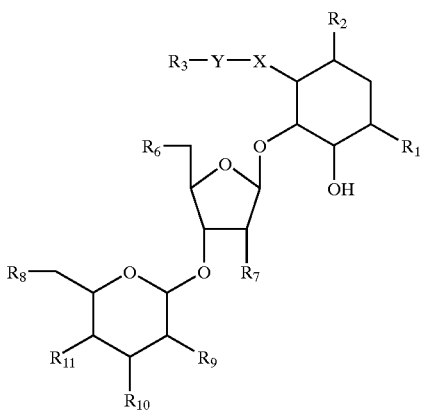
(IX)

wherein
X is O, S, or NH;
Y is a bond or a divalent linking group; and
$R_3$ is aryl or heteroaryl;
or $R_3$ is a substituted aryl or a substituted heteroaryl having at least one substituent group selected from the list consisting of OH, SH, Cl, F, Br, I, CN, $NH_2$, $NO_2$, amidine, guanidine, COOH, $C_{1-8}$ alkyl, $C_{2-8}$ alkenyl, alkynyl, $CF_3$, $OCF_3$, saturated or unsaturated carbocycle, saturated or unsaturated heterocycle, aryl, heteroaryl, $OR_{14}$, $SR_{14}$, $NHR_{14}$, $N(R_{14})_2$, $C(S)R_{14}$, $C(O)R_{14}$, $C(O)NHR_{14}$, $C(O)OR_{14}$, $OC(O)R_{14}$, wherein $R_{14}$ is hydrogen, $C_{1-8}$ alkyl, $C_{2-8}$ alkenyl, $C_{2-8}$ alkynyl, carbocyclic, heterocyclic, aryl or a heteroaryl group.

15. The process of claim 14 further comprising the step of isolating the compound of formula VIII from a mixture comprising said compounds of formulas VIII and IX.

16. A process according to claim 14, wherein said compound of formula (VI) is neomycin B.

* * * * *

UNITED STATES PATENT AND TRADEMARK OFFICE
CERTIFICATE OF CORRECTION

| | | |
|---|---|---|
| PATENT NO. | : 6,967,242 B2 | Page 1 of 1 |
| APPLICATION NO. | : 10/299220 | |
| DATED | : November 19, 2002 | |
| INVENTOR(S) | : Eric E. Swayze et al. | |

It is certified that error appears in the above-identified patent and that said Letters Patent is hereby corrected as shown below:

1) Column 1, line 7, please insert

-- STATEMENT OF FEDERALLY SPONSORED RESEARCH

This work reported was made with United States Government support under DARPA contract N65236-99-1-5419. The United States Government may have certain rights to the invention.--.

Signed and Sealed this

Twenty-eighth Day of November, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,967,242 B2 | Page 1 of 1 |
| APPLICATION NO. | : 10/299220 | |
| DATED | : November 22, 2005 | |
| INVENTOR(S) | : Eric E. Swayze et al. | |

It is certified that error appears in the above-identified patent and that said Letters Patent is hereby corrected as shown below:

1) Column 1, line 7, please insert

-- STATEMENT OF FEDERALLY SPONSORED RESEARCH

This work reported was made with United States Government support under DARPA contract N65236-99-1-5419. The United States Government may have certain rights to the invention.--.

This certificate supersedes Certificate of Correction issued November 28, 2006.

Signed and Sealed this

Second Day of January, 2007

JON W. DUDAS
*Director of the United States Patent and Trademark Office*